United States Patent [19]

Feit

[11] 3,985,777

[45] Oct. 12, 1976

[54] SULPHAMYL-BENZOIC ACID DERIVATIVES

[75] Inventor: Peter Werner Feit, Gentofte, Denmark

[73] Assignee: Lovens Kemiske Fabrik Produktionsaktieselskab, Ballerup, Denmark

[22] Filed: Nov. 15, 1973

[21] Appl. No.: 416,164

Related U.S. Application Data

[62] Division of Ser. No. 887,409, Dec. 22, 1969, Pat. No. 3,806,534.

[52] U.S. Cl. .......................... 260/347.2; 260/243 B; 260/247.1 R; 260/247.1 L; 260/268 R; 260/268 H; 260/268 FT; 260/293.67; 260/293.68; 260/247.1 S; 260/293.69; 260/293.7; 260/247.1 M; 260/293.71; 260/293.73; 260/294.8 F; 260/302 R; 260/302 H; 260/309; 260/247.1 P; 260/309.2; 260/326.82; 260/332.2 A; 260/347.7; 260/465 D; 260/470; 260/501.12; 260/501.13; 260/518 R; 260/518 A; 260/519; 260/558 S; 424/285; 424/275

[51] Int. Cl.$^2$ ....................................... C07D 307/38

[58] Field of Search ......... 260/347.2, 347.7, 501.12, 260/501.13, 465, 470

[56] References Cited

UNITED STATES PATENTS

| | | | |
|---|---|---|---|
| 3,238,203 | 3/1966 | Krapcho | 260/347.2 |
| 3,567,714 | 3/1971 | Wilson | 260/347.7 |

OTHER PUBLICATIONS

Cutting, "Handbook of Pharm.," 4th ed., (1969), pp. 284, 285.

*Primary Examiner*—James O. Thomas, Jr.
*Assistant Examiner*—A. Siegel
*Attorney, Agent, or Firm*—Dennis P. Clarke

[57] ABSTRACT

This invention relates to new, therapeutically active compounds of the general formula

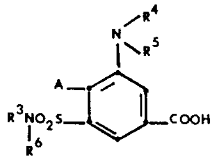

in which A represents one of the groupings

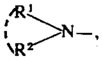 $R^2$—O—, $R^2$—S—, $R^2$—OS—, and $R^2$—$O_2$S—, $R^1$, $R^2$, $R^3$, and $R^4$ each represents hydrogen, an aliphatic radical, a cycloaliphatic radical, or an aromatically, cycloaliphatically, or heterocyclically substituted aliphatic radical, in addition to which $R^2$ and $R^3$ may each represent an aromatic or heterocyclic radical, and when A is

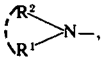

$R^1$ and $R^2$ may be linked to form a 5- to 8-membered heterocyclic ring system, which may have one or more nitrogen atoms, sulphur atoms, or oxygen atoms in addition to the nitrogen atom linked to $R^1$ and $R^2$; $R^5$ is hydrogen or lower alkyl; and $R^6$ is hydrogen or lower alkyl or acyl; to salts, esters, and amides of the said compounds; and to methods for the production of the compounds.

1 Claim, No Drawings

SULPHAMYL-BENZOIC ACID DERIVATIVES

This is a Division, of application Ser. No. 887,409 filed Dec. 22, 1969 now U.S. Pat. No. 3,806,534.

This invention relates to a series of new compounds, and to methods for the production of the compounds.

The new compounds have the general formula

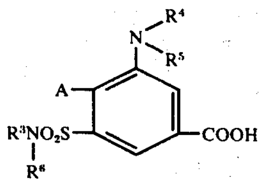

(I)

in which A stands for

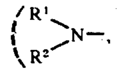

$R^2$—O—, $R^2$—S—, $R^2$—OS—, or $R^2$—$O_2$S—, and $R^1$, $R^2$, $R^3$, and $R^4$ each represents an aliphatic radical, a cycloaliphatic radical, or an aromatically, cycloaliphatically or heterocyclically substituted aliphatic radical; in addition $R^2$ and $R^3$ may each represent an aromatic or heterocyclic radical; and when A is

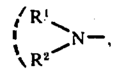

$R^1$ and $R^2$ together with the nitrogen atom can represent a heterocyclic ring system with from 5 to 8 ring members, and which may have additionally one or more nitrogen, oxygen, or sulphur atoms in the ring; $R^5$ represents a lower alkyl radical, and $R^6$ represents a lower alkyl radical or an acyl group; $R^1$, $R^3$, $R^4$, $R^5$, and $R^6$ may also be each a hydrogen atom. The invention further comprises salts, esters, and amides of the compounds of formula I.

In particular, each of $R^1$, $R^2$, $R^3$, and $R^4$ may represent a straight or branched, saturated or unsaturated, alkyl radical, e.g. a methyl, ethyl, propyl, isopropyl, butyl, isobutyl, or tert. butyl radical, or one of the different isomeric pentyl, hexyl, or heptyl radicals, an alkenyl or alkynyl radical, e.g. a vinyl, allyl, or propargyl radical, a cycloalkyl or cycloalkenyl radical, e.g. a cyclopropyl, cyclobutyl, cyclopentyl, cyclohexyl, cycloheptyl, or cyclooctyl radical, or one of the different isomeric cyclopentenyl or cyclohexenyl radicals, or an adamantyl radical. The aliphatic radicals may further contain hetero atoms, e.g. oxygen, sulphur, or nitrogen, which may interrupt the carbon chain, and may be further substituted, e.g. with lower alkyl radicals. In the aromatically, cycloaliphatically or heterocyclically substituted aliphatic radicals, the aromatic part of the radical can be a mono- or bicyclic aryl radical, e.g. a phenyl or naphthyl radical, the cycloaliphatic part of the radical can be one of the cycloalkyl or cycloalkenyl radicals mentioned above, the heterocyclic part of the radical can be a mono- or bicyclic radical containing one or more oxygen, sulphur, and nitrogen atoms as ring members, e.g. 2-, 3-, or 4-pyridyl, 2- or 3-furyl or -thienyl, thiazolyl, imidazolyl, benzimidazolyl, and the corresponding hydrogenated ring systems, and the aliphatic part of the radicals can contain 1 to 4 carbon atoms. Illustrative examples of such aromatically or heterocyclically substituted aliphatic radicals are benzyl, 1- or 2-phenylethyl, 1- or 2-naphthyl-methyl, furylmethyl, and the corresponding ethyl, propyl, and butyl radicals. When, additionally, $R^2$ and $R^3$ represent aromatic or heterocyclic radicals these can be the mono- or bicyclic radicals already mentioned above.

When A represents

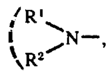

and $R^1$ and $R^2$ together with the nitrogen atom represent a heterocyclic ring system, this stands particularly for a saturated or unsaturated heterocyclic ring optionally containing one or more nitrogen, oxygen, or sulphur atoms, such as piperidyl, morpholinyl, thiomorpholinyl, pyrrolidyl, imidazolyl, thiazolidyl, piperazinyl etcetera radicals. When $R^6$ represents an acyl group, it is preferably a lower aliphatic acyl group, e.g. an acetyl or propionyl group.

All the above mentioned radicals can be substituted in different positions with different groups, such as one or more halogen atoms, e.g. chlorine or bromine atoms, with an alkyl or halo-alkyl group, e.g. trifluoromethyl, with carboxy, carbalkoxy, or carbamyl radicals, di-lower alkylamino radicals, or hydroxy groups, which may be etherified or esterified, with etherified mercapto groups, or with sulphonamide groups.

The salts of the compounds of the invention are pharmaceutically acceptable salts, and include, for example, alkali metal salts, alkaline earth metal salts, the ammonium salt, or amine salts formed, for instance, from mono-, di-, or trialkylamines, from mono-, di-, or trialkanolamines, or from cyclic amines. The esters of the compounds are preferably derived from substituted or unsubstituted lower aliphatic alcohols, phenols, or aralkyl alcohols, e.g. the methyl ester, the cyanomethyl ester, the phenyl ester, and the benzyl ester.

The compounds of the invention possess valuable therapeutic properties and have, according to animal experiments performed in connection with the present invention, a particularly strong effect as diuretics and saluretics, the ratio between the excretion of sodium ions and potassium ions being very favourable. Furthermore the compounds are not carboanhydrase inibitors, and these facts in connection with a favourable therapeutic index and a low toxicity make the present compounds particularly valuable.

The effect of the present compounds is surprising in respect to the disclosure in the specification of our Belgian Pat. No. 716,122 as it was not to be foreseen that the halogen substituent in the neighbouring position to the sulphonamide group could be replaced with the result that compounds with even stronger activity were obtained.

Illustrative examples of compounds of formula I having a particularly strong effect are compounds where A is as defined above and where $R^1$, $R^3$, and $R^5$ are hydrogen, $R^2$ is a substituted or unsubstituted phenyl group, $R^4$ is an alkyl radical having from 3 to 6 carbon atoms, or a benzyl, furfuryl, or thienylmethyl radical, $R^6$ is hydrogen, a methyl group or lower aliphatic acyl group, and the methyl esters of these compounds.

The present compounds are effective after oral, enteral or parenteral administration, and for therapeutic purposes they are preferably formulated as tablets, pills, dragees, or capsules containing the free acid of salts thereof with atoxic bases, or the esters or amides thereof, mixed with carriers and/or auxiliary agents.

Pharmaceutical organic or inorganic, solid or liquid carriers suitable for oral, enteral, or parenteral administration can be used to make up compositions containing the present compounds. Gelatine, lactose, starch, magnesium stearate, talc, vegetable and animal fats and oils, gum, polyalkylene glycol, or other known carriers for medicaments are all suitable as carriers.

The compositions may further contain other therapeutic compounds applied in the treatment of, for example oedemas and hypertension, besides the well known auxiliary agents. Such other compounds may be, for instance, Veratrum- or Rauwolfia alkaloids, e.g. reserpine, rescinnamine, or protoveratrine, or synthetic hypotensive compounds, e.g. hydralazine, or other diuretics and saluretics, such as the well-known benzothiadiazines, e.g. hydroflumethiazide, bendroflumethiazide, and the like. Potassium-sparing diuretics, e.g. triamterene, may also be used in the preparation of the compositions. For some purposes it may be desirable to add small amounts of carboanhydrase inhibitors or aldosterone antagonists, e.g. spironolactone.

Salts, which are soluble in water, may with advantage be administered by injection. The pharmaceutical preparations are useful in the treatment of oedematous conditions, e.g. cardiac, hepatic, renal, lung and brain oedema, or oedematous conditions during pregnancy, in the treatment of pathological conditions which produce an abnormal retention of the electrolytes of the body, and in the treatment of hypertension.

Another object of the invention resides in the selection of a dose of one of the new compounds, and its salts which can be administered so that the desired activity is achieved without simultaneous secondary effects. It has been found that the compounds and their salts are conveniently administered in dosage units containing not less than 0.1 mg, and up to 25 mg, preferably from 0.25 to 2.5 mg, calculated as the free acid of formula I.

By the term "dosage unit" is meant a unitary, i.e. a single dose which is capable of being administered to a patient, and which may be readily handled and packed, remaining as a physically stable unit dose comprising either the active material as such or a mixture of it with solid or liquid pharmaceutical diluents or carriers.

If the composition is to be injected, a sealed ampoule, a vial or a similar container may be provided containing a parenterally acceptable aqueous or oily injectable solution or dispersion of the active material as the dosage unit.

The parenteral preparations are useful in particular in the treatment of conditions where a quick dehydration is desirable, e.g. in the intensive therapy applied in the case of oedemas in the lung. In the continuous therapy of patients suffering from e.g. hypertension, the tablets or capsules may be the appropriate form of pharmaceutical preparation owing to the prolonged effect obtained when the drug is given orally, in particular in the form of sustained-release tablets.

In the treatment of heart failure and hypertension, such tablets may advantageously contain other active components, as specified hereinbefore.

The present compounds may be provided by various methods. In one embodiment of the invention a compound of the general formula

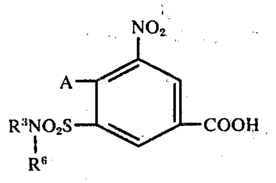

(IV)

in which A, $R^3$, and $R^6$ are as hereinbefore defined, or a salt, an ester, or an amide thereof, is subjected to a reduction, for example by catalytic hydrogenation using a noble metal catalyst, to yield the compounds of the invention, in which $R^4$ and $R^5$ are hydrogen atoms. In some cases, for instance when the substituents would be affected by a catalytic hydrogenation, other reducing agents, such as sodium dithionite or metallic iron, may be preferred. The compounds so obtained, preferably in the form of a salt or an ester, can be monoalkylated by reaction with a compound of the formula $R^4X$, $R^4$ being as defined hereinbefore, and X being a halogen atom, preferably chlorine or bromine, a hydroxyl group, or a sulphonyloxy group, an alkyl- or arylsulphonyloxy group, the carboxylic acid group subsequently being liberated, if desired. The $R^5$ group can subsequently be introduced by an ordinary alkylation process or by a reductive alkylation in known manner.

In another embodiment, a 3-amino-4-A-5-$R^3R^6$-sulphamyl-benzoic acid or an ester or amide thereof is subjected to reductive alkylation, using in the reaction an aldehyde, which is capable of introducing the corresponding $R^4$ substituent; on the other hand the esters and amides can be prepared as the last step from the carboxylic acid of formula I, and the $R^6$-substituent may be introduced as an intermediary step, or as a last step.

The different steps of the process are standard procedures including reductive alkylation, hydrogenation, esterification, amidation, using a reactive derivative of the corresponding carboxylic acid, or hydrolysis, and the reaction conditions may vary according to the starting products and the substituents of the reacting compounds. The compounds are obtained in free form or in form of their salts, esters or amides depending upon the conditions under which the reaction is performed.

The starting material of formula IV is prepared according to the following reaction scheme:

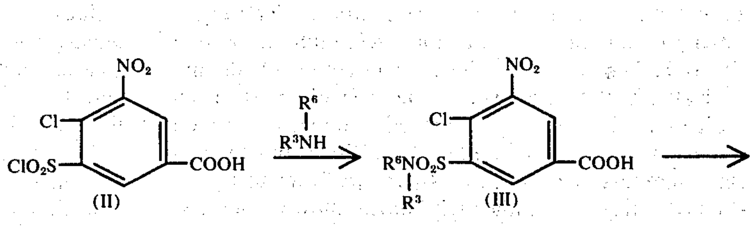

(II) (III)

-continued

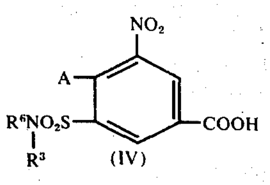

(IV)

in which formulae A and $R^3$ have the meanings before defined and $R^6$ is a lower alkyl, the compound III being used either as the free carboxylic acid or in the form of salt, or an ester, in which latter case the compound IV is also obtained as an ester, which, if desired, may be hydrolyzed. In the case, where $R^6$ is an acyl group, the compounds of formula IV can be provided by acylation of the corresponding compounds in which $R^6$ is hydrogen.

If desired, the carboxylic acid group of the compounds of formula IV can be amidated using a reactive derivative thereof, e.g. an acid halide.

The starting materials of formula II and of formula III, in which $R^3$ and $R^6$ are hydrogen atoms, are described in the specification of our Belgian Patent No. 716,122.

The N-substituted sulphamyl derivatives of formula III are generally prepared by treating a compound of formula II with an amine

$R^3$ being different from hydrogen, and $R^6$ being an alkyl group or hydrogen, preferably under mild conditions, i.e. at low temperature and without an excess of the amine

and usually in the presence of a base which is not capable of being alkylated and which is used as an acceptor for the acid liberated by the process.

The reaction product of formula III, or an ester or an amide thereof, is treated with a compound of the formula A—H, A being as defined above, i.e. with an amine, an alcohol, a thioalcohol, a phenol, a thiophenol, or a sulphinic acid to form a compound of formula IV, or the corresponding ester. In the case where A stands for

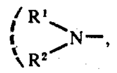

A—H is used in the reaction in the form of the free amine, in the case where A stands for $R^2$—O—, $R^2$—S—, or $R^2—O_2S$—, reaction conditions are used in which the ionic form of A is present or in which A is an alcoholate, thioalcoholate, phenolate, or thiophenolate, or a sulphinate, respectively. Water, ethanol, aqueous alcohols, or alcohols of the formula $R^2$—OH—, wherein $R^2$ is as hereinbefore defined, as well as other suitable solvents may, if desired, be used as reaction media in this process, and the reaction temperature depends on the reactants used.

In the case where A stands for

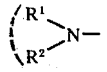

and is identical with

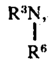

the compound of formula II can be transformed in one step into a compound of formula IV, using not less than two equivalents of the amine

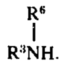

The compounds of formula IV, A being $R^2$—S—, can furthermore be converted to the corresponding sulphinyl or sulphonyl derivatives by oxidation, e.g. with hydrogen peroxide, the amount of peroxide and the reaction conditions being decisive for the degree of the oxidation, whereafter the compounds of formula I can be obtained as described above.

In another embodiment of the method for the preparation of the compounds of the invention in which A stands for $R^2$—OS— and $R^2—O_2S$—, the compounds can also be and are preferably prepared from the corresponding compounds of formula I in which A is $R^2$—S— by oxidation with, for instance, hydrogen peroxide. Depending upon the amount of hydrogen peroxide and the reaction conditions used, the oxidation results in the sulphinyl or the sulphonyl derivatives. These oxidations can be performed on the free carboxylic acids as well as on salts, on esters, or on amides thereof. In the case where a carboxylic acid derivative is obtained, the free carboxylic acid may be liberated subsequently by well-known processes, if desired. Compounds of the invention, in which the substituents are unsaturated, may be hydrogenated or transformed by addition-reactions into other compounds of the invention, and further substituents in $R^2$ and in $R^4$ may be introduced or removed on any reaction step.

The invention will now be described by the following examples which are only illustrative and are not to be limiting:

EXAMPLE 1

3-Amino-4-phenoxy-5-sulphamyl-benzoic acid

A. 3-Nitro-4-phenoxy-5-sulphamyl-benzoic acid

A mixture of 4-chloro-6-nitro-5-sulphamyl-benzoic acid (140 g), phenol (100 g), sodium bicarbonate (170 g), and water (1,000 ml) was heated to 85° C while stirring and kept at this temperature for 16 hours. After cooling to 4° C, the precipitated sodium salt of 3-nitro-4-phenoxy-5-sulphamyl-benzoic acid was filtered off and washed with ice-water. The sodium salt was dissolved in boiling water (3000 ml), and the 3-nitro-4-phenoxy-5-sulphamyl-benzoic acid was precipitated by the addition of 4N hydrochloric acid. After cooling, the acid was isolated by suction and dried. The melting point was 255°–256° C.

B. 3-Amino-4-phenoxy-5-sulphamyl-benzoic acid

A suspension of 3-nitro-4-phenoxy-5-sulphamyl-benzoic acid (20 g) in water (100 ml) was adjusted to a pH of 8 by the addition of 1N lithium hydroxide. The resulting solution was hydrogenated at room temperature and 1.1 atmosphere hydrogen pressure, using a palladium-on-carbon catalyst (0.6 g catalyst containing 10% Pd). After the hydrogen uptake had become negligible, the catalyst was removed by filtration, and the 3-amino-4-phenoxy-5-sulphamyl-benzoic acid was precipitated from the filtrate by the addition of 4N hydrochloric acid until the pH was 2.5. After recrystallization from aqueous ethanol and drying, the melting point was 255°–256° C.

EXAMPLE 2

3-Amino-5-methylsulphamyl-4-phenoxy-benzoic acid

A. 5-Methylsulphamyl-3-nitro-4-phenoxy-benzoic acid

By substituting 4-Chloro-5-methylsulphamyl-3-nitro-benzoic acid (147 g) for 4-chloro-3-nitro-5-sulphamyl-benzoic acid and following the procedure of Example 1 A, the above 3-nitro-compound was obtained with a melting point of 219°–222° C.

The above starting material is new and was prepared in the following manner:

To a mixture of 1N sodium hydroxide (60 ml) and aqueous methylamine (3.43 g containing 1.2 g of methylamine) 4-chloro-5-chlorosulphonyl-3-nitro-benzoic acid (9.3 g) was added in portions, while stirring and keeping the mixture at 0°–3° C. Then the reaction mixture was left standing until it had reached room temperature, after which the 4-chloro-5-methylsulphamyl-3-nitro-benzoic acid was precipitated by slow acidification with 4N hydrochloric acid. The precipitate was collected by suction and recrystallized from aqueous ethanol. The melting point was 228°–229° C.

B. 3-Amino-5-methylsulphamyl-4-phenoxy-benzoic acid

By substituting 5-methylsulphamyl-3-nitro-4-phenoxy-benzoic acid for 3-nitro-4-phenoxy-5-sulphamyl-benzoic acid and following the procedure of Example 1 B, the above compound was obtained with a melting point of 283° C.

EXAMPLE 3

3-Amino-5-dimethylsulphamyl-4-phenoxy-benzoic acid

A. 5-Dimethylsulphamyl-3-nitro-4-phenoxy-benzoic acid

A mixture of 4-chloro-5-dimethylsulphamyl-3-nitro-benzoic acid (3.08 g), a phenol (2g), sodium hydrogen carbonate (3.4 g), and water (20 ml) was heated at 90° C for 8 hours. Then water (40 ml) was added and, after cooling, the 5-dimethylsulphamyl-3-nitro-4-phenoxy-benzoic acid was precipitated by acidification with 4N hydrochloric acid. After isolation by filtration and several recrystallizations from ethanol, the said compound was obtained with a melting point of 224°–226° C.

B. 3-Amino-5-dimethylsulphamyl-4-phenoxy-benzoic acid

Following the procedure of Example 1 B and substituting 5-dimethylsulphamyl-3-nitro-4-phenoxy-benzoic acid for 3-nitro-4-phenoxy-5-sulphamyl-benzoic acid, the above compound was obtained with a melting point of 211°–212° C.

By substituting 5-n-butylsulphamyl-4-chloro-3-nitro-benzoic acid (2.36 g) for the 4-chloro-5-dimethylsulphamyl-3-nitro-benzoic acid of Example 3 A, 5-n-butylsulphamyl-3-nitro-4-phenoxy-benzoic acid was obtained with a melting point of 191°–192° C.

By substituting 5-n-butylsulphamyl-3-nitro-4-phenoxy-benzoic acid for 3-nitro-4-phenoxy-5-sulphamyl-benzoic acid in Example 1 B, 3-amino-5-n-butylsulphamyl-5-phenoxy-benzoic acid was obtained as a hemi-hydrate with a melting point of 188°–189° C.

The starting materials, 4-chloro-5-dimethylsulphamyl-3-nitro-benzoic acid and 5-n-butylsulphamyl-4-chloro-3-nitro-benzoic acid, were new and were obtained as described for the starting material of Example 2 by substituting aqueous dimethylamine (3.6 g containing 1.5 g of dimethylamine) and n-butylamine (2.2 g), respectively, for the aqueous methylamine, and had melting points of 233–235° C, and 196–198° C, respectively.

EXAMPLE 4

3-Amino-4-anilino-5-phenylsulphamyl-benzoic acid and sodium salt

A. 4-Anilino-3-nitro-5-phenylsulphamyl-benzoic acid

To a solution of 4-chloro-3-nitro-5-chlorosulphonyl-benzoic acid (6 g) in ethyl acetate (50 ml), aniline (7.5 g) was added, while stirring. The reaction mixture was stirred for a further 8 hours and filtered. The filtrate was evaporated, and the residue was dissolved in a mixture of aqueous sodium hydrogen carbonate and diethyl ether. The aqueous layer was separated, and the 4-anilino-3-nitro-5-phenylsulphamyl-benzoic acid was precipitated by addition of 4N hydrochloric acid. After recrystallization from aqueous ethanol (25% ethanol in water), the melting point was 249°–250° C.

B. 3-Amino-4-anilino-5-phenylsulphamyl-benzoic acid and sodium salt

A suspension of 4-anilino-3-nitro-5-phenylsulphamyl-benzoic acid (2 g) in water (15 ml) was adjusted to pH 8 by means of 1N sodium hydroxide, and the resulting solution was hydrogenated after addition of Pd (0.15 g) on carbon powder catalyst (10%). After the hydrogen uptake had become negligible, the reaction mixture was heated to 95° C, and the catalyst was removed by filtration. After cooling, the precipitated sodium salt of 3-amino-4-anilino-5-phenylsulphamyl-benzoic acid was collected by filtration.

1.5 g of the sodium salt of 3-amino-4-anilino-5-phenylsulphamyl-benzoic acid was dissolved in hot water (50 ml). 1N hydrochloric acid was added until pH 2, and the mixture was cooled. The precipitated 3-amino-4-anilino-5-phenylsulphamyl-benzoic acid was collected, recrystallized from aqueous methanol, and dried in vacuo at 78° C. The crystalline compound contained 1 molecule of water of crystallization. The melting point was 222°–223° C.

EXAMPLE 5

3-Amino-4-(p-methoxyphenoxy)-5-sulphamyl-benzoic acid

A. 4-(p-Methoxyphenoxy)-3-nitro-5-sulphamyl-benzoic acid

A mixture of 4-chloro-3-nitro-5-sulphamyl-benzoic acid (14 g), p-methoxyphenol (9.3 g), and 1N sodium bicarbonate (200 ml) was stirred at 90° C for 5 hours.

After cooling, the resulting 4-(p-methoxyphenoxy)-3-nitro-5-sulphamyl-benzoic acid was precipitated by the addition of 4N hydrochloric acid until the pH was 1, and collected by suction. The crude acid was dissolved in hot methanol (100 ml) and precipitated by the addition of water (100 ml) and cooling. After collection and drying in vacuo, the melting point was 229°–230° C.

B. 3-Amino-4-(p-methoxyphenoxy)-5-sulphamyl-benzoic acid

By substituting 4-(p-methoxyphenoxy)-3-nitro-5-sulphamyl-benzoic acid (7 g) for the 3-nitro-4-phenoxy-5-sulphamyl-benzoic acid of Example 1 B, the above compound was obtained with a melting point of 260°–261° C.

EXAMPLE 6

3-Amino-5-sulphamyl-4-(m-trifluoromethylphenoxy)-benzoic acid

A. 3-Nitro-5-sulphamyl-4-(m-trifluoromethylphenoxy)-benzoic acid

A mixture of 4-chloro-3-nitro-5-sulphamyl-benzoic acid (7 g), m-trifluoromethylphenol (20 g), and 1N sodium bicarbonate (100 ml) was stirred at 95° C for 6 hours. Then the reaction mixture was acidified by the addition of 4N hydrochloric acid and the excess of trifluoromethylphenol was removed by steam distillation. After cooling, the precipitated 3-nitro-5-sulphamyl-4-(m-trifluoromethylphenoxy)-benzoic acid was collected by suction and recrystallized several times from methanol-water. The melting point of the pure compound was 205°–206° C.

B. 3-Amino-5-sulphamyl-4-(m-trifluoromethylphenoxy)-benzoic acid

By substituting 3-nitro-5-sulphamyl-4-(m-trifluoromethylphenoxy)-benzoic acid for the 3-nitro-4-phenoxy-5-sulphamyl-benzoic acid of Example 1 B, the above compound was obtained with a melting point of 270° C.

EXAMPLE 7

3-Amino-4-(m-chlorophenoxy)-5-sulphamyl-benzoic acid

A. 4-(m-Chlorophenoxy)-3-nitro-5-sulphamyl-benzoic acid

A mixture of 4-chloro-3-nitro-5-sulphamyl-benzoic acid (28 g), m-chlorophenol (26 g), sodium bicarbonate (34 g), and water (200 ml) was stirred at 85° C for 10 hours. After cooling, excess m-chlorophenol was removed by extraction with diethyl ether, and 4-(m-chlorophenoxy)-3-nitro-5-sulphamyl-benzoic acid was precipitated from the aqueous layer by the addition of 4N hydrochloric acid. After recrystallization from aqueous methanol, the melting point was 230°–232° C.

B. 3-Amino-4-(m-chlorophenoxy)-5-sulphamyl-benzoic acid

A mixture of ammonium chloride (1.2 g), metallic iron powder (11 g), concentrated hydrochloric acid (0.05 ml), and water (30 ml) was heated on a steam bath. 4-(m-Chlorophenoxy)-3-nitro-5-sulphamyl-benzoic acid (3 g) was added while stirring, and the heating was continued for 6 hours. Then 1N sodium hydroxide (50 ml) was added, and the reaction mixture was filtered. The filter cake was washed twice with 1N sodium hydroxide (50 ml each time). The combined filtrates were adjusted to a pH of 2.5 by the addition of 4N hydrochloric acid. After cooling, the precipitated 3-amino-4-(m-chlorophenoxy)-5-sulphamyl-benzoic acid was collected by suction, and recrystallized from aqueous ethanol. The melting point was 239°–240°C.

EXAMPLE 8

3-Amino-4-methoxy-5-sulphamyl-benzoic acid

A. 4-Methoxy-3-nitro-5-sulphamyl-benzoic acid (14 g) was added to a solution of sodium methoxide, prepared from sodium (6.9 g) and methanol (200 ml). The reaction mixture was refluxed for 5 hours and evaporated in vacuo. The residue was dissolved in water (100 ml) and conc. hydrochloric acid was added (50 ml). The precipitated 4-methoxy-3-nitro-5-sulphamyl-benzoic acid was recrystallized from water. The melting point was 200°–201° C.

B. 3-Amino-4-methoxy-5-sulphamyl-benzoic acid

4-Methoxy-3-nitro-5-sulphamyl-benzoic acid (2.8 g) was dissolved in 1N sodium hydrogen carbonate solution (12 ml), and hydrogenated, using Pd-on-carbon as a catalyst, and the 3-amino-4-methoxy-5-sulphamyl-benzoic acid was isolated as described in EXample 1 B. After several recrystallizations from water and drying at 78° C in vacuo, the melting point was 210° C under decomposition.

EXAMPLE 9

3-Amino-4-anilino-5-sulphamyl-benzoic acid

A. 4-Anilino-3-nitro-5-sulphamyl-benzoic acid

A mixture of 4-Chloro-3-nitro-5-sulphamyl-benzoic acid (8.4 g), aniline (8.4 g), and water (40 ml) was stirred at 80° C for 2 hours. After the addition of 1N hydrochloric acid (50 ml) and cooling, the precipitated 4-anilino-3-nitro-5-sulphamyl-benzoic acid was collected by suction, washed with water, and recrystallized from aqueous ethanol. The melting point was 261°–262° C.

B. 3-Amino-4-anilino-5-sulphamyl-benzoic acid

A suspension of 4-anilino-3-nitro-5-sulphamyl-benzoic acid (7 g) in water (80 ml) was adjusted to a pH of 9 by the addition of 2N sodium hydroxide or lithium hydroxide, and the resulting solution was hydrogenated at room temperature and 1.1 atmospheres hydrogen pressure after the addition of a palladium-on-carbon catalyst (0.3 g catalyst containing 10% Pd). After the hydrogen uptake had become negligible, the catalyst was removed by filtration, and the 3-amino-4-anilino-5-sulphamyl-benzoic acid was precipitated from the filtrate by addition of 4N hydrochloric acid until the pH was 2.5. After recrystallization from aqueous ethanol and drying in vacuo, the melting point was 251° C.

EXAMPLE 10

3-Amino-5-sulphamyl-4-(m-toluidino)-benzoic acid

A. 3-Nitro-5-sulphamyl-4-(m-toluidino)-benzoic acid

A mixture of 4-chloro-3-nitro-5-sulphamyl-benzoic acid (28 g), m-toluidine (32.2 g), and water (500 ml) was refluxed for 3 hours. After cooling and acidification with 2N hydrochloric acid, the precipitated 3-nitro-5-sulphamyl-4-(m-toluidino)-benzoic acid was collected by suction, washed with water, and recrystallized from isopropanol. After drying at 115° C in vacuo, the melting point was 256°–259° C.

B. 3-Amino-5-sulphamyl-4-(m-toluidino)-benzoic acid

By substituting 3-nitro-5-sulphamyl-4-(m-toluidino)-benzoic acid for the 4-anilino-3-nitro-5-sulphamyl-benzoic acid of Example 9 B, the above compound was obtained with a melting point of 280°–282° C after recrystallization from ethanol.

EXAMPLE 11

3-Amino-5-sulphamyl-4-(p-toluidino)-benzoic acid

A. 3-Nitro-5-sulphamyl-4-(p-toluidino)-benzoic acid

By substituting p-toluidine for m-toluidine in Example 10 A, the above compound was obtained with a melting point of 252°–253° C, after recrystallization from ethanol and drying.

B. 3-Amino-5-sulphamyl-4-(p-toluidino)-benzoic acid

By substituting 3-nitro-5-sulphamyl-4-(p-toluidino)-benzoic acid for the 4-anilino-3-nitro-5-sulphamyl-benzoic acid of Example 9 B, the above compound was obtained with a melting point of 249°–252° C.

EXAMPLE 12

3-Amino-5-sulphamyl-4-(o-toluidino)-benzoic acid

A. 3-Nitro-5-sulphamyl-4-(o-toluidino)-benzoic acid

By substituting o-toluidine for m-toluidine in Example 10 A, the above compound was obtained with a melting point of 251–252° C.

B. 3-Amino-5-sulphamyl-4-(o-toluidino)-benzoic acid

By substituting 3-nitro-5-sulphamyl-4(o-toluidino)-benzoic acid for the 4-anilino-3-nitro-5-sulphamyl-benzoic acid of Example 9 B, the above compound was obtained.

EXAMPLE 13

3-Amino-4-(o-methoxyanilino)-5-sulphamyl-benzoic acid

A. 4-(o-Methoxyanilino)-3-nitro-5-sulphamyl-benzoic acid

By substituting o-anisidine (37 g) for m-toluidine in Example 10 A, the above compound was obtained with a melting point of 207°–208° C after recrystallization from ethanol and drying in vacuo.

B. 3-Amino-4-(o-methoxyanilino)-5-sulphamyl-benzoic acid

By substituting 4-(o-methoxyanilino)-3-nitro-5-sulphamyl-benzoic acid for the 4-anilino-3-nitro-5-sulphamyl-benzoic acid of Example 9 B, the above compound was obtained after recrystallization from aqueous ethanol.

EXAMPLE 14

3-Amino-4-(m-methoxyanilino)-5-sulphamyl-benzoic acid

A. 4-(m-Methoxyanilino)-3-nitro-5-sulphamyl-benzoic acid

By substituting m-anisidine (37 g) for m-toluidine in Example 10 A, the above compound was obtained with a melting point of 253°–254° C.

B. 3-Amino-4-(m-methoxyanilino)-5-sulphamyl-benzoic acid

By substituting 4-(m-methoxyanilino)-3-nitro-5-sulphamyl-benzoic acid for the 4-anilino-3-nitro-5-sulphamyl-benzoic acid of Example 9 B, the above compound was obtained with a melting point of 232°–234° C after recrystallization from aqueous methanol.

EXAMPLE 15

3-Amino-4-(p-methoxyanilino)-5-sulphamyl-benzoic acid

A. 4-(p-Methoxyanilino)-3-nitro-5-sulphamyl-benzoic acid

By substituting p-anisidine (37 g) for m-toluidine in Example 10 A, the above compound was obtained with a melting point of 246° C (decomp.).

B. 3-Amino-4-(p-methoxyanilino)-5-sulphamyl-benzoic acid

By substituting 4-(p-methoxyanilino)-3-nitro-5-sulphamyl-benzoic acid for the 4-anilino-3-nitro-5-sulphamyl-benzoic acid of Example 9 B, the above compound was obtained with a melting point of 214°C.

EXAMPLE 16

3-Amino-5-sulphamyl-4-(m-trifluoromethylanilino)-benzoic acid

A. 3-Nitro-5-sulphamyl-4-(m-trifluoromethylanilino)-benzoic acid

By substituting m-trifluoromethylaniline (49.5 g) for m-toluidine in Example 10 A and extending the reaction time to 7 hours, the above compound was obtained after the cooled reaction mixture had been acidified and diluted with ethanol (150 ml). After recrystallization from aqueous ethanol, the melting point was 213°–215° C.

B. 3-Amino-5-sulphamyl-4-(m-trifluoromethylanilino)-benzoic acid

By substituting 3-nitro-5-sulphamyl-4-(m-trifluoromethylanilino)-benzoic acid for the 4-anilino-3-nitro-5-sulphamyl-benzoic acid of Example 9 B, the above compound was obtained with a melting point of 273°–274° C.

EXAMPLE 17

3-Amino-4-(2,4-dimethylanilino)-5-sulphamyl-benzoic acid

A. 4-(2,4-Dimethylanilino)-3-nitro-5-sulphamyl-benzoic acid

By substituting 2,4-dimethylaniline (36.5 g) for m-toluidine in Example 10 A, the above compound was obtained with a melting point of 224°–226° C after recrystallization from ethanol and drying. The compound crystallized with one molecule of ethanol.

B. 3-Amino-4-(2,4-dimethylanilino)-5-sulphamyl-benzoic acid

By substituting 3-nitro-5-sulphamyl-4-(2,4-dimethylanilino)-benzoic acid for the 4-anilino-3-nitro-5-sulphamyl-benzoic acid of Example 9 B, the above compound was obtained with a melting point of 241°–241.5° C after recrystallization from ethanol.

EXAMPLE 18

3-Amino-4-(p-chloroanilino)-5-sulphamyl-benzoic acid

A. 4-(p-Chloroanilino)-3-nitro-5-sulphamyl-benzoic acid

By substituting p-chloroaniline (39 g) for m-toluidine in Example 10 A, the above compound was obtained with a melting point of 241°–243° C after recrystallization from ethanol and drying in vacuo.

B. 3-Amino-4-(p-chloroanilino)-5-sulphamyl-benzoic acid

A mixture of 4-(p-chloroanilino)-3-nitro-5-sulphamyl-benzoic acid (7.43 g), water (50 ml), and concentrated aqueous ammonia (15 ml) was stirred at 25° C, and a solution of sodium dithionite (13.5 g) in water (50 ml) was added dropwise. After 1 hour, the pH of the reaction mixture was adjusted to 2.5, and the precipitated reaction product was filtered off. After repeated recrystallizations from aqueous ethanol, and after drying for 4 hours in vacuo, 3-amino-4-(p-chloroanilino)-5-sulphamyl-benzoic acid was obtained with a melting point of 273°–274° C.

EXAMPLE 19

3-Amino-4-(p-hydroxyanilino)-5-sulphamyl-benzoic acid

A. 4-(p-Hydroxyanilino)-3-nitro-5-sulphamyl-benzoic acid

By substituting p-aminophenol (24.5 g) for m-toluidine in Example 10 A, the above compound was obtained with a melting point of 262° C (decomp.) after recrystallization from aqueous ethanol and water.

B. 3-Amino-4-(p-hydroxyanilino)-5-sulphamyl-benzoic acid

By substituting 4-(p-hydroxyanilino)-3-nitro-5-sulphamyl-benzoic acid (10 g) for the 3-nitro-4-phenoxy-5-sulphamyl-benzoic acid of Example 1 B, the above compound was obtained with a melting point of 296° C (decomp.).

EXAMPLE 20

3-Amino-4-cyclohexylamino-5-sulphamyl-benzoic acid

A. 4-Cyclohexylamino-3-nitro-5-sulphamyl-benzoic acid

By substituting cyclohexylamine (30 g) for m-toluidine in Example 10 A, the above compound was obtained with a melting point of 185°–186° C after recrystallization from aqueous ethanol and drying in vacuo.

B. 3-Amino-4-cyclohexylamino-5-sulphamyl-benzoic acid

By substituting 4-cyclohexylamino-3-nitro-5-sulphamyl-benzoic acid (15 g) for the 3-nitro-4-phenoxy-5-sulphamyl-benzoic acid of Example 1 B, the above compound was obtained with a melting point of 233° C (decomp.)

EXAMPLE 21

3-Amino-4-benzylamino-5-sulphamyl-benzoic acid

A. 4-Benzylamino-3-nitro-5-sulphamyl-benzoic acid

A mixture of 4-chlor-3-nitro-5-sulphamyl-benzoic acid (8.4 g), benzylamine (12.84 g), and water (40 ml) was stirred at room temperature for 3 hours. After standing for 30 minutes, the liquor was decanted off, water (100 ml) was added, and 4-benzylamino-3-nitro-5-sulphamyl-benzoic acid was precipitated by the addition of 4N hydrochloric acid. After collection and recrystallization from aqueous methanol, the melting point was 188° C (decomp.).

B. 3-Amino-4-benzylamino-5-sulphamyl-benzoic acid

By substituting 4-benzylamino-3-nitro-5-sulphamyl-benzoic acid for the 4-anilino-3-nitro-5-sulphamyl-benzoic acid of Example 9 B, the above compound was obtained with a melting point of 218°–219° C after recrystallization from aqueous methanol.

EXAMPLE 22

3-Amino-4-($\beta$-phenylethylamino)-5-sulphamyl-benzoic acid

A. 3-Nitro-4-($\beta$-phenylethylamino)-5-sulphamyl-benzoic acid

A mixture of 4-chloro-3-nitro-5-sulphamyl-benzoic acid (22.4 g), $\beta$-phenylethylamine (29 g), and water (200 ml) was refluxed for 2.5 hours. After cooling, the reaction mixture was adjusted to a pH of 9.5 and extracted with diethyl ether. The aqueous layer was then acidified by addition of 4N hydrochloric acid, and the precipitated 3-nitro-4-($\beta$-phenylethylamino)-5-sulphamyl-benzoic acid was collected by suction. After recrystallization from aqueous ethanol, the melting point was 208°–208.5° C.

B. 3-Amino-4-($\beta$-phenylethylamino)-5-sulphamyl-benzoic acid

By substituting 3-nitro-4-($\beta$-phenylethylamino)5-sulphamyl-benzoic acid for the 4-anilino-3-nitro-5-sulphamyl-benzoic acid of Example 9 B, the above compound was obtained with a melting point of 194°–195° C.

EXAMPLE 23

3-Amino-4-(p-carboxyanilino)-5-sulphamyl-benzoic acid

A. 4-(p-Carboxylanilino)-3-nitro-5-sulphamyl-benzoic acid

A suspension of 4-chloro-3-nitro-5-sulphamyl-benzoic acid (22.4 g) and p-aminobenzoic acid (10.95 g) in water was adjusted to a pH of 7 by the addition of sodium bicarbonate. The resulting solution was refluxed for 10 hours. After acidifying with 4N hydrochloric acid and cooling, the precipitated 4-(p-carboxyanilino)-3-nitro-5-sulphamyl-benzoic acid was collected by suction and recrystallized from aqueous ethanol. The melting point was 297° C (decomp.). The compound contained one molecule of water of crystallization.

B. 3-Amino-4-(p-carboxyanilino)-5-sulphamyl-benzoic acid

By substituting 4-(p-carboxyanilino)-3-nitro-5-sulphamyl-benzoic acid for the 4-anilino-3-nitro-5-sulphamyl-benzoic acid of Example 9 B, the above compound was obtained with a melting point of 262° C (decomp.) after drying in vacuo at 115°C.

EXAMPLE 24

3-Amino-4-(2-methoxyethylamino)-5-sulphamyl-benzoic acid

A. 4-(2-Methoxyethylamino)-3-nitro-5-sulphamyl-benzoic acid

A mixture of 4-chloro-3-nitro-5-sulphamyl-benzoic acid (4.2 g), 2-methoxyethylamine (5.6 g), and 50% ethanol (10 ml) was heated to 60° C for 1 hour. The ethanol was distilled off under reduced pressure, and the resulting 4-(2-methoxyethylamino)-3-nitro-5-sulphamyl-benzoic acid was precipitated by addition of 4N hydrochloric acid until pH 2. After recrystallization from water, the melting point was 192°–194° C. The compound crystallized with 1 molecule of water of crystallization.

B. 3-Amino-4-(2-methoxyethylamino)-5-sulphamyl-benzoic acid 4-(2-Methoxyethylamino)-3-nitro-5-sulphamyl-benzoic acid (3.2 g) was dissolved in 1N sodium hydroxide (10 ml) and hydrogenated after addition of moist Raney-Nickel (1 g). When the hydrogen uptake had become negligible, the catalyst was removed by filtration, and the resulting 3-amino-4-(2-methoxyethylamino)-5-sulphamyl-benzoic acid was precipitated from the filtrate by addition of 4N hydrochloric acid until pH 3. After recrystallization from water, the melting point was 209°–211° C.

EXAMPLE 25

3-Amino-4-isopropylamino-5-sulphamyl-benzoic acid

A. 4-Isopropylamino-3-nitro-5-sulphamyl-benzoic acid

Isopropylamine (120 ml) and water 8 ml) were added to 4-chloro-3-nitro-5-sulphamyl-benzoic acid (22.4 g), while cooling. Then the reaction mixture was stirred for 5 days at room temperature. After evaporation in vacuo, the residue was triturated with 4N hydrochloric acid, after which the resulting 4-isopropylamino-3-nitro-5-sulphamyl-benzoic acid was collected by suction. After recrystallization from aqueous ethanol, the acid was obtained with a melting point of 206°C (decomp.).

B. 3-Amino-4-isopropylamino-5-sulphamyl-benzoic acid

By substituting 4-isopropylamino-3-nitro-5-sulphamyl-benzoic acid for the 4-anilino-3-nitro-5-sulphamyl-benzoic acid of Example 9 B, the above compound was obtained with a melting point of 226° C (decomp.).

EXAMPLE 26

3-Amino-4-(N-methyl-ethanolamino)-5-sulphamyl-benzoic acid

A. 4-(N-Methyl-ethanolamino)-3-nitro-5-sulphamyl-benzoic acid

A mixture of 4-chloro-3-nitro-5-sulphamyl-benzoic acid (14 g), 2-methylamino-ethanol (19 g), and 50% ethanol (30 ml) in water was stirred at 50° C for 2 hours. After addition of water (100 ml), 1N hydrochloric acid was added until pH 2, causing precipitation of 4-(N-methyl-ethanolamino)-3-nitro-5-sulphamyl-benzoic acid. After recrystallization from water, the melting point was 125°–127° C.

B. 3-Amino-4-(N-methyl-ethanolamino)-5-sulphamyl-benzoic acid 4-(N-Methyl-ethanolamino)-3-nitro-5-sulphamyl-benzoic acid (9 g) was dissolved in water by adjusting the pH to 8 by means of 1N sodium hydroxide. Raney-Nickel catalyst (1 g) was added, and the solution was hydrogenated until the hydrogen uptake had become negligible. The catalyst was removed by filtration, and the resulting 3-amino-4-(N-methyl-ethanolamino)-5-sulphamyl-benzoic acid was precipitated from the filtrate by addition of 4N hydrochloric acid until pH 2.5. After recrystallization from water, the melting point was 209°–211° C.

EXAMPLE 27

3-Amino-4-piperidino-5-sulphamyl-benzoic acid

A. 3-Nitro-4-piperidino-5-sulphamyl-benzoic acid

A mixture of 4-chloro-3-nitro-5-sulphamyl-benzoic acid (2.8 g), piperidine (3.4 g), and water (13 ml) was stirred at 95° C for 2 hours. Then the reaction mixture was adjusted to a pH of 2.5 by the addition of 4N hydrochloric acid, and the precipitated 3-nitro-4-piperidino-5-sulphamyl-benzoic acid was collected and recrystallized from aqueous methanol. The melting point was 237°–238° C (decomp.)

B. 3-Amino-4-piperidino-5-sulphamyl-benzoic acid

By substituting 3-nitro-4-piperidino-5-sulphamyl-benzoic acid for the 4-anilino-3-nitro-5-sulphamyl-benzoic acid of Example 9 B, the above compound was obtained with a melting point of 279° C (decomp.) after recrystallization from aqueous methanol.

EXAMPLE 28

3-Amino-4-morpholino-5-sulphamyl-benzoic acid

A. 4-Morpholino-3-nitro-5-sulphamyl-benzoic acid

By substituting morpholine (3.48 g) for piperidine in Example 27 A, the above compound was obtained with a melting point of 273° C (decomp.).

B. 3-Amino-4-morpholino-5-sulphamyl-benzoic acid

By substituting 4-morpholino-3-nitro-5-sulphamyl-benzoic acid for the 4-anilino-3-nitro-5sulphamyl-benzoic acid of Example 9 B, the above compound was obtained with a melting point of 297° C (decomp.) after recrystallization from aqueous methanol.

EXAMPLE 29

3-Amino-4-(3-dimethylaminopropylamino)-5-sulphamyl-benzoic acid

A. 4-(3-dimethylaminopropylamino)-3-nitro-5-sulphamyl-benzoic acid

To a suspension of 4-chloro-3-nitro-5-sulphamyl-benzoic acid (22.4 g) in water (24 ml), 3-dimethylaminopropylamine (120 ml) was added, while cooling. Then the reaction mixture was heated to 100° C and kept at this temperature for 2 hours. After cooling and evaporating in vacuo to dryness, the residue was dissolved in water (80 ml) and adjusted to a pH of 7.5 by addition of 4N hydrochloric acid. The precipitated 4-(3-dimethylaminopropylamino)-3-nitro-5-sulphamyl-benzoic acid was collected by suction and recrystallized from water. The melting point was 262° C (decomp.).

B. 3-Amino-4-(3-dimethylaminopropylamino)-5-sulphyamyl-benzoic acid 4-(3-Dimethylaminopropylamino)-3-nitro-5-sulphamyl-benzoic acid (6.92 g) was dissolved in 2N sodium hydroxide (25 ml), and the solution was hydrogenated at room temperature and 1.1 atmospheres hydrogen pressure after the addition of a palladium-on-carbon catalyst (0.35 g catalyst containing 10% Pd.). After the hydrogen uptake had become negligible, the catalyst was removed by filtration, and the filtrate was adjusted to a pH of 8 by addition of 4N hydrochloric acid. The precipitated 3-amino-4-(3-dimethylamino-propylamino)-5-sulphamyl-benzoic acid was collected by suction and recrystallized from water. After drying in vacuo at 115° C for 2 hours, the melting point was 264° C (decomp.).

EXAMPLE 30

3-Amino-4-(β-naphthylamino)-5-sulphamyl-benzoic acid

A. 4-(β-Naphthylamino)-3-nitro-5-sulphamyl-benzoic acid

A mixture of 4-chloro-3-nitro-5-sulphamyl-benzoic acid (28 g), β-naphthylamine (43.2 g), dry ethanol (250 ml), and dry sodium acetate (8.2 g) was refluxed for 5 hours. Then the reaction mixture was evaporated in vacuo, and the residue was triturated with warm 1N hydrochloric acid (350 ml). The precipitated 4-(β-naphthylamino-3-nitro-5-sulphamyl-benzoic acid was filtered off and recrystallized from aqueous ethanol. The compound was obtained as a monohydrate and had a melting point of 262° C (decomp.).

B. 3-Amino-4-(β-naphthylamino)-5-sulphamyl-benzoic acid

By substituting 4-(β-naphthylamino)-3-nitro-5-sulphamyl-benzoic acid for the 4-anilino-3-nitro-5-sulphamyl-benzoic acid of Example 9 B, the above compound was obtained with a melting point of 245° C.

EXAMPLE 31

3-Amino-4-phenylthio-5-sulphamyl-benzoic acid

A. 3-Nitro-4-phenylthio-5-sulphamyl-benzoic acid

A mixture of 4-chloro-3-nitro-5-sulphamyl-benzoic acid (28 g), thiophenol (10.25 ml), and 1N sodium bicarbonate (300 ml) was refluxed for 3 hours. After cooling, the precipitated sodium salt of 3-nitro-4-phenylthio-5-sulphamyl-benzoic acid was filtered off. The sodium salt was dissolved in hot water (200 ml), and 3-nitro-4-phenylthio-5-sulphamyl-benzoic acid was precipitated by the addition of 4N hydrochloric acid until the pH was 1. After isolation and recrystallization from aqueous ethanol, the acid was obtained with a melting point of 245°–247° C.

B. 3-Amino-4-phenylthio-5-sulphamyl-benzoic acid

A mixture of ammonium chloride (2.4 g), metallic iron powder (24 g), concentrated hydrochloric acid (0.1 ml), and water (60 ml) was heated to 90° C with stirring, and 3-nitro-4-phenylthio-5-sulphamyl-benzoic acid (10 g) was added in small portions during 2 hours. The reaction mixture was stirred on a steam bath for an additional 2 hours. After the addition of dilute sodium hydroxide until the pH was 8, the hot reaction mixture was filtered, and the filter-cake was washed with warm dilute sodium hydroxide. After the addition of 4N hydrochloric acid to the filtrate until its pH was 2and cooling the resulting precipitate, consisting of 3-amino-4-phenylthio-5-sulphamyl-benzoic acid, was filtered off and dried at 78° C in vacuo. The melting point was 285° C.

EXAMPLE 32

3-Amino-4-n-butylthio-5-sulphamyl-benzoic acid

A. 4-n-Butylthio-3-nitro-5-sulphamyl-benzoic acid and sodium salt

A mixture of 4-chloro-3-nitro-5-sulphamyl-benzoic acid (28 g), butylmercaptan (11 ml), and 1N sodium bicarbonate (300 ml) was stirred at 90° C for 22 hours. After cooling, the precipitated sodium salt of 4-n-butylthio-3-nitro-5-sulphamyl-benzoic acid was filtered off. The salt was dissolved in hot water, and the acid was precipitated by addition of 4N hydrochloric acid. After cooling, the acid was isolated and recrystallized from aqueous ethanol. The melting point was 173°–174° C.

B. 3-Amino-4-butylthio-5-sulphamyl-benzoic acid

To a solution of sodium dithionite (15.9 g) in aqueous ammonia (13 g $NH_3$ in 150 ml water) 4-n-butylthio-3-nitro-5-sulphamyl-benzoic acid (8.35 g) was added in portions during 1 hour, while stirring. The reaction mixture was then heated on a steam bath for 30 minutes. Hydrochloric acid was added until the pH was 1, and heating was continued for 1 hour. After cooling, the pH was adjusted to 3 by the addition of 2N sodium hydroxide, and isopropanol (25 ml) was added. The precipitated 3-amino-4-n-butylthio-5-sulphamyl-benzoic acid was filtered off and recrystallized from aqueous ethanol. The melting point was 223°–224° C.

EXAMPLE 33

3-Amino-5-sulphamyl-4(o-tolylthio)-benzoic -(o-tolyl-thio)-benzoic

A. 3-Nitro-5-sulphamyl-4-(o-tolythio)-benzoic acid

A mixure of 4-chloro-3-nitro-5-sulphamyl-benzoic acid (28 g), o-thiocresol (12.4 g), and 1N sodium bicarbonate (300 ml) was refluxed for 3 hours. After cooling, the precipitated sodium salt of 3-nitro-5-sulphamyl-4-o-tolylthio-benzoic acid was filtered off and washed with 1N sodium bicarbonate solution. The sodium salt was dissolved in hot water (250 ml), and the acid was precipitated by the addition of 4N hydrochloric acid (17 ml). After isolation, recrystallization from aqueous ethanol, and drying at 115° C and 10 mm Hg for 3 hours. The acid was obtained with a melting point of 165°–166° C.

B. 3-Amino-5-sulphamyl-4-(o-tolylthio)-benzoic acid

By substituting 3-nitro-5-sulphamyl-4-(o-tolylthio)-benzoic acid (7.7 g) for the 4-butylthio-3-nitro-5-sulphamyl-benzoic acid of Example 32 B, 3-amino-5-sulphamyl-4-(o-tolylthio)-benzoic acid was obtained with a melting point of 277° C.

EXAMPLE 34

3-Amino-4-phenylsulphonyl-5-sulphamyl-benzoic acid

A. 3-Nitro-4-phenylsylphonyl-5-sulphamyl-benzoic acid

A mixture of 4-chloro-3-nitro-5-sulphamyl-benzoic acid (24 g), benzenesulphinic acid (13 g), sodium acetate (16 g), and anhydrous ethanol (65 ml) was stirred at 78° C for 20 hours. After cooling, the precipitated sodium salt of 3-nitro-4-phenylsulphonyl-5-sulphamyl-benzoic acid was collected by suction. The sodium salt was dissolved in aqueous ethanol, and the acid was precipitated by acidification with 4N hydrochloric acid. After collection by suction and recrystallization from aqueous ethanol, the 3-nitro-4-phenylsulphonyl-5-sulphamyl-benzoic acid had a melting point of 291° C (decomp.).

B. 3-Amino-4-phenylsulphonyl-5-sulphamyl-benzoic acid

A suspension of 3-nitro-4-phenylsulphonyl-5-sulphamyl-benzoic acid (6 g) in water (300 ml) was hydrogenated at room temperature and 1.1 atmospheres hydrogen pressure after addition of Pd-on-carbon catalyst (0.3 g catalyst containing 10% Pd). After the hydrogen uptake had become negligible, the reaction mixture was neutralized by addition of 2N sodium hydroxide, and the catalyst was removed from the resulting suspension by filtration. The filtrate was adjusted to a pH of 2.5 by addition of 4N hydrochloric acid, and the precipitated 3-amino-4-phenylsulphonyl-5-sulphamyl-benzoic acid was collected by suction. After recrystallization from aqueous ethanol, the acid had a melting point of 278° C (decomp.).

EXAMPLE 35

3-Amino-4-n-butylsulphinyl-5-sulphamyl-benzoic acid

A. 4-n-Butylsulphinyl-3-nitro-5-sulphamyl-benzoic acid

To a solution of 4-n-butylthio-3-nitro-5-sulphamyl-benzoic acid (10 g) in acetic acid (150 ml), perhydrol (30 ml of 30% hydrogen peroxide in water) was added, while stirring. After additional stirring for 24 hours at room temperature, the reaction mixture was diluted with water (150 ml) and left standing for 8 hours. The precipitated 4-n-butylsulphinyl-3-nitro-5-sulphamyl-benzoic acid was collected by suction, recrystallized from aqueous ethanol, and dried in vacuo. The acid was obtained as a semi-hydrate with a melting point of 165° C (decomp.).

B. 3-Amino-4-n-butylsulphinyl-5-sulphamyl-benzoic acid

To a solution of sodium dithionite (7.3 g) in water (50 ml) conc. aqueous ammonia (25 ml) was added, after which 4-n-butylsulphinyl-3-nitro-5-sulphamyl-benzoic acid (4 g) was added in portions at 25° C, while stirring. The reaction mixture was heated on a steam bath for 30 minutes. Then 4N hydrochloric acid was added until a pH of 1, while the heating was continued. After the evolution of sulphur dioxide had ceased, the reaction mixture was adjusted to a pH of 2.5 by addition of 2N sodium hydroxide, and cooled. The precipitated 3-amino-4-n-butylsulphinyl-5-sulphamyl-benzoic acid was collected by suction, recrystallized from aqueous ethanol, and dried in vacuo at 115° C. The acid was obtained with a melting point of 237° C (decomp.).

EXAMPLE 36

3-Amino-5-sulphamyl-4-($\beta,\beta,\beta$-trifluoroethoxy)-benzoic acid

A. 3-Nitro-5-sulphamyl-4-($\beta,\beta,\beta$-trifluoroethoxy)-benzoic acid

To a solution of sodium $\beta,\beta,\beta$-trifluoroethoxide in $\beta,\beta,\beta$-trifluoroethanol (prepared by dissolving 2.1 g of sodium in 45 ml of $\beta,\beta,\beta$-trifluoroethanol), 4-chloro-3-nitro-5-sulphamyl-benzoic acid (4.2 g) was added, and the resulting solution was refluxed for 5 days. After evaporation of the reaction mixture in vacuo, water (50 ml) was added, and the aqueous solution was acidified with 4N hydrochloric acid. After standing in a refrigerator, the precipitate was collected by suction. After several recrystallizations from aqueous ethanol, the 3-nitro-5-sulphamyl-4-($\beta,\beta,\beta$-trifluoroethoxy)-benzoic acid was obtained with a melting point of 195°–197° C.

B. 3-Amino-5-sulphamyl-4-($\beta,\beta,\beta$-trifluoroethoxy)-benzoic acid

3-Nitro-5-sulphamyl-4-($\beta,\beta,\beta$-trifluoroethoxy)-benzoic acid (2g) in water (30 ml) was adjusted to a pH of 9 by addition of lithium hydroxide, and the resulting solution was hydrogenated at room temperature and at a hydrogen pressure of 1.1 atmospheres after addition of Pd-on-carbon catalyst (0.2 g catalyst containing 10% Pd). After the hydrogen uptake had become negligible, the catalyst was removed by filtration, and the 3-amino-5-sulphamyl-4-($\beta,\beta,\beta$-trifluoroethoxy)-benzoic acid was precipitated from the filtrate by addition of 4N hydrochloric acid until a pH of 2.5. After recrystallization from aqueous ethanol and drying, the melting point of the compound was 253°–254° C.

EXAMPLE 37

3-Amino-4-(2-methyl-6-pyridylamino)-5-sulphamyl-benzoic acid

A. Ethyl-4-chloro-3-nitro-5-sulphamyl-benzoate

A solution of 4-chloro-3-nitro-5-sulphamyl-benzoic acid (28 g) in dry ethanol (250 ml) was saturated with gaseous hydrogen chloride. The reaction mixture was allowed to warm during the inlet of the hydrogen chloride. After standing for 3 hours, the solvent was removed by evaporation in vacuo. The residue was dissolved in a mixture of diethyl ether and dilute sodium hydrogen carbonate. The organic layer was separated, washed with water and dried. The diethyl ether was distilled off, and the residue was recrystallized from dry ethanol, yielding the ethyl-4-chloro-3-nitro-5-sulphamyl-benzoate with a melting point of 154° C.

B. Ethyl-4-(2-methyl-6-pyridylamino)-3-nitro-5-sulphamyl-benzoate

A mixture of ethyl-4-chloro-3-nitro-5-sulphamyl-benzoate (3.08 g) and 6-amino-2-methyl-pyridine (3.24 g) was melted on an oil bath at 140° C and kept at this temperature for 2 hours, while stirring. The still warm reaction mixture was triturated with ethanol (35 ml) and after cooling, the ethyl-4-(2-methyl-6-pyridylamino)-3-nitro-5-sulphamyl-benzoate was collected by suction and washed with ethanol. After recrystallization from acetonitrile, the compound had a melting point of 203°–204° C.

C. 4-(2-Methyl-6-pyridylamino)-3-nitro-5-sulphamyl-benzoic acid

Ethyl-4-(2-methyl-6-pyridylamino)-3-nitro-5-sulphamyl-benzoate (2 g) was dissolved in 1N sodium hydroxide (30 ml) and heated on a steam bath for 1 hour. After cooling, water (50 ml) was added, and the pH of the reaction mixture was adjusted to 4.5 by addition of 1N hydrochloric acid. The precipitated 4-(2-methyl-6-pyridylamino)-3-nitro-5-sulphamyl-benzoic acid was collected by suction, washed with water, and dried. The compound had a melting point of 305° C (decomp.).

D. 3-Amino-4-(4-methyl-6-pyridylamino)-5-sulphamyl-benzoic acid

A suspension of 4-(2-methyl-6-pyridylamino)-5-sulphamyl-benzoic acid (4 g) in water (20 ml) was adjusted to pH 8 by addition of 1N lithium hydroxide, and the resulting solution was hydrogenated at room temperature and at a hydrogen pressure of 1.1 atmospheres after addition of a Pd-on-carbon catalyst (0.2 g catalyst containing 10% Pd). After the hydrogen uptake had become negligible, the catalyst was removed by filtration, and the 3-amino-4-(2-methyl-6-pyridylamino)-5-sulphamyl-benzoic acid was precipitated from the filtrate by addition of 4N hydrochloric acid until a pH of 5. After recrystallization from aqueous ethanol and drying in vacuo, the melting point of the compound was 256° C decomp).

EXAMPLE 38

3-Amino-4-(4-benzyloxyphenoxy)-5-sulphamyl-benzoic acid

A. n-Butyl-4-chloro-3-nitro-5-sulphamyl-benzoate

A mixture of 4-chloro-3-nitro-5-sulphamyl-benzoic acid (10 g), n-butanol (100 ml), and conc. sulphuric acid (2ml) was refluxed for 4 hours, during which 50 ml of the solvent were distilled off slowly. After cooling, the n-butyl-4-chloro-3-nitro-5-sulphamyl-benzoate was isolated by filtration and recrystallized from n-butanol. The compound was obtained with a melting point of 140°–141° C.

B. n-Butyl-4-(4-benzyloxyphenoxy)-3-nitro-5-sulphamyl-benzoate

To a solution of sodium n-butoxide in n-butanol (prepared from 0.074 g of sodium and 16 ml of dry n-butanol), 4-benzyloxyphenol (0.64 g), and n-butyl-4-chloro-3-nitro-5-sulphamyl-benzoate were added. The reaction mixture was refluxed for 4 hours and cooled, whereafter the precipitated n-butyl-4-(4-benzyloxyphenoxy)-3-nitro-5-sulphamyl-benzoate was isolated and recrystallized from n-butanol. After drying, the compound was obtained with a melting point of 138°–144° C.

C. 4-(4-benzyloxyphenoxy)-3-nitro-5-sulphamyl-benzoic acid

A solution of n-butyl-4-(4-benzyloxyphenoxy)-3-nitro-5-sulphamyl-benzoate (7.3 g) in 1N sodium hydroxide (120 ml) was heated on a steam bath for 45 minutes. After cooling and acidification by addition of 4N hydrochloric acid, the precipitated 4-(4-benzyloxyphenoxy)-3-nitro-5-sulphamyl-benzoic acid was isolated by filtration and recrystallized from aqueous ethanol. After drying, the compound was obtained with a melting point of 247° C.

D. 3-Amino-4-(4-benzyloxyphenoxy)-5-sulphamyl-benzoic acid

A suspension of 4-(4-benzyloxyphenoxy)-3-nitro-5-sulphamyl-benzoic acid (10 g) in water (250 ml) was adjusted to pH 11 by addition of 1N sodium hydroxide. The resulting solution was hydrogenated at room temperature and at 1.1 atmospheres hydrogen pressure after addition of a platinum oxide catalyst (0.4 g). After the hydrogen uptake had become negligible, the catalyst was removed by filtration, and the 3-amino-4-(4-benzyloxyphenoxy)-5-sulphamyl-benzoic acid was precipitated by adjusting the filtrate to pH 2.5 by addition of 4N hydrochloric acid. After recrystallization from aqueous ethanol and drying, the compound was obtained with a melting point of 264°–265° C.

EXAMPLE 39

3-Amino-4-phenoxy-5-sulphamyl-benzoic acid

A. 3-Nitro-4-phenoxy-5-sulphamyl-benzoyl chloride

A mixture of 3-nitro-4-phenoxy-5-sulphamyl-benzoic acid (5 g) and thionyl chloride (50 ml) was heated on a steam bath for 5 hours. After evaporation in vacuo to dryness, the compound was obtained as a crude product, which was used in the next step without further purification.

B. 3-Nitro-4-phenoxy-5-sulphamyl-benzamide

3-Nitro-4-phenoxy-5-sulphamyl-benzoyl chloride (4 g) was added in portions to liquid ammonia (40 ml). Then excess of ammonia was distilled off, and the residue was triturated with water (50 ml). The precipitated 3-nitro-4-phenoxy-5-sulphamyl-benzamide was isolated by filtration and recrystallized twice from aqueous ethanol. After drying in vacuo, the compound was obtained with a melting point of 255°–256° C.

C. 3-Amino-4-phenoxy-5-sulphamyl-benzamide

To a suspension of 3-nitro-4-phenoxy-5-sulphamyl-benzamide (2.4 g) in water (25 ml) 1N lithium hydroxide (10 ml) was added. The resulting solution was hydrogenated at room temperature and at 1.1 atmospheres hydrogen pressure after addition of Pd-on-carbon catalyst (0.2 g catalyst containing 10% Pd). After the hydrogen uptake had become negligible, the catalyst was removed by filtration, and the filtrate was then adjusted to pH 7.5 by addition of 4N hydrochloric acid. The precipitated 3-amino-4-phenoxy-5-sulphamyl-benzamide was isolated and dried in vacuo. The compound was obtained with a melting point of 291°–292° C.

D. 3-Amino-4-phenoxy-5-sulphamyl-benzoic acid

A mixture of 3-amino-4-phenoxy-5-sulphamyl-benzamide (1 g) and 1N sodium hydroxide (20 ml) was refluxed for 1 hour. After cooling, the 3-amino-4-phenoxy-5-sulphamyl-benzoic acid was precipitated from the reaction mixture by addition of 4N hydrochloric acid until pH 2.5. After several recrystallizations from aqueous ethanol and drying, the compound was obtained with a melting point of 252°–253° C.

EXAMPLE 40

3-Amino-5-acetylsulphamyl-4-phenoxy-benzoic acid

A. 5-Acetylsulphamyl-3-nitro-4-phenoxy-benzoic acid

3-Nitro-4-phenoxy-5-sulphamyl-benzoic acid (10 g) was dissolved in water (250 ml) by adjusting the pH to 8 by addition of 1N lithium hydroxide. Then acetic anhydride (12 g) was added dropwise, while stirring and keeping the pH constant at pH 9 by means of 1N lithium hydroxide, using an automatic titrator. After the acetic anhydride was consumed, the reaction mixture was acidified by addition of 4N hydrochloric acid. The precipitated 5-acetylsulphamyl-3-nitro-4-phenoxy-benzoic acid was isolated by filtration and recrystallized from aqueous ethanol. The compound with a melting point of 270°–271° C.

B. 3-Amino-5-acetylsulphamyl-4-phenoxy-benzoic acid

By substituting 5-acetylsulphamyl-3-nitro-4-phenoxy-benzoic acid for the 3-nitro-4-phenoxy-5-sulphamyl-benzoic acid of Example 1B, the above compound was obtained as a monohydrate with a melting point of 290°–293° C.

EXAMPLE 41

3-n-Butylamino-4-phenoxy-5-sulphamyl-benzoic acid and its sodium salt

To a suspension of 3-amino-4-phenoxy-5-sulphamyl-benzoic acid (10 g) in n-butanol (200 ml) concentrated sulphuric acid (2ml) was added, while stirring. The reaction mixture was heated under reflux at such conditions that the water formed during the reaction was separated. When the NMR-spectrum of a sample of the reaction mixture diluted with n-butanol showed at the two doublets of the aromatic protons of the ring carrying the sulphamyl group that more than 90% of the formed butyl-3-amino-4-phenoxy-5-sulphamyl-benzoate intermediate was converted into the corresponding 3-n-butylamino-benzoate, which caused a frequence shift to a higher field, 2N sodium hydroxide (200 ml) was added, and the boiling was continued for 45 minutes. After this saponification, the reaction mixture was neutralized to a pH of 8 by the addition of concentrated hydrochloric acid. After cooling, the sodium salt precipitated. It was filtered off and recrystallized from water (100 ml). The sodium salt, which crystallized with 3 molecules of water of crystallization, was then dissolved in boiling water (200 ml). 1N Hydrochloric acid was added until the pH was 2.5, and, after cooling, the precipitated 3-n-butylamino-4-phenoxy-5-sulphamyl-benzoic acid was collected by filtration. After recrystallization from aqueous ethanol and drying, the pure compound was obtained with a melting point of 230°–231° C.

EXAMPLE 42

Ethanolamine salt of 3-n-butylamino-4-phenoxy-5-sulphamyl-benzoic acid 3-n-Butylamino-4-phenoxy-5-sulphamyl-benzoic acid (1.82 g) was dissolved in boiling ethanol (20 ml) and a solution of ethanolamine (0.3 g) in ethanol (15 ml) was added. After cooling, the precipitated ethanolamine salt was collected by filtration and recrystallized from ethanol. The melting point was 194°–195° C.

EXAMPLE 43

Potassium salt of 3-n-butylamino-4-phenoxy-5-sulphamyl-benzoic acid

The ethanolamine salt of 3-n-butylamino-4-phenoxy-5-sulphamyl-benzoic acid (10 g) was dissolved in boiling water (50 ml), and aqueous saturated potassium chloride (5 ml) was added. After cooling, the precipitated potassium salt was collected by filtration and recrystallized from water. The salt was obtained as a hydrate.

EXAMPLE 44

Neutral calcium salt of 3-n-butylamino-4-phenoxy-5-sulphamyl-benzoic acid

The ethanolamine salt of 3-n-butylamino-4-phenoxy-5-sulphamyl-benzoic acid (4.25 g) was dissolved in water (150 ml), and an aqueous solution of calcium chloride (2 ml containing 40% $CaCl_2$) was added, while stirring. The precipitated calcium salt was collected by suction and dried. The salt contained 3.5 molecules of water of crystallization.

EXAMPLE 45

Methyl-3-n-butylamino-4-phenoxy-5-sulphamyl-benzoate

A mixture of 3-n-butylamino-4-phenoxy-5-sulphamyl-benzoic acid (3 g) and methanol (60 ml) was saturated with gaseous hydrogen chloride. The reaction mixture was allowed to warm during the saturation. After cooling and standing for 5 hours, the reaction mixture was evaporated in vacuo, and the residue was recrystallized from methanol (12 ml), whereby the methyl-3-n-butylamino-4-phenoxy-5-sulphamyl-benzoate was obtained with a melting point of 148° C.

EXAMPLE 46

Cyanomethyl-3n-butylamino-4-phenoxy-5-sulphamyl-benzoate

A mixture of 3-n-butylamino-4-phenoxy-5-sulphamyl-benzoic acid (1 g), chloroacetonitrile (0.625 g), triethylamine (0.28 g), and dry acetone (10 ml) was refluxed for 19 hours. After cooling, the precipitated triethylamine hydrochloride was removed by filtration, and the filtrate was evaporated in vacuo. To the residue, water (20 ml) and ethylacetate (50 ml) were added, and the pH of the aqueous layer was adjusted to pH 7.5. The organic layer was then separated, washed with dilute sosium hydrogen carbonate, dried, and evaporated in vacuo. The residue was recrystallized several times from chloroform/petroleum ether. Thereby the cyanomethyl-3-n-butylamino-4-phenoxy-5-sulphamyl-benzoate was obtained with a melting point of 159°–161° C.

EXAMPLE 47

3-Butylamino-4-(4-sulphamylphenoxy)-5-sulphamyl-benzoic acid

To chlorosulphuric acid (5 ml), 3-butylamino-4-phenoxy-5-sulphamyl-benzoic acid (1 g) was added in portions, while stirring and keeping the temperature below 45° C. The reaction mixture was stirred to 10 minutes and then poured into ice water (10 g of ice and 20 ml of water). The precipitated 3-butylamino-4-(4-chlorosulphonylphenoxy)-5-sulphamyl-benzoic acid was isolated by filtration and without further purification added to aqueous ammonia (10 ml containing 2.5 g of ammonia). Excess of ammonia was removed by evaporation, and the resulting solution was adjusted to pH 2.5 by addition of 4N hydrochloric acid. The precipitated 3-butylamino-4-(4-sulphamylphenoxy)-5-sulphamyl-benzoic acid was isolated by filtration, recrystallized from aqueous ethanol, and dried. The obtained compound had a melting point of 265° C.

EXAMPLE 48

3-n-Butylmethylamino-4-phenoxy-5-sulphamyl-benzoic acid

A suspension of 3-n-butylamino-4-phenoxy-5-sulphamyl-benzoic acid (1 g) of aqueous ethanol (20 ml of ethanol and 20 ml of water) containing formaldehyde (0.35 g) was hydrogenated at room temperature and at 1.1 atmospheres hydrogen pressure after addition of Pd-on-carbon powder (0.1 g catalyst containing 10% of Pd). When the hydrogen uptake had become negligible, the reaction mixture was warmed to 60° C, and the catalyst was filtered off. After addition of water (15 ml) to the filtrate and cooling, the precipitated 3-n-butylmethylamino-4-phenoxy-5-sulphamyl-benzoic acid was collected by filtration and recrystallized from aqueous ethanol. After drying in vacuo at 115° C, the compound was obtained with a melting point of 159°–162° C.

EXAMPLE 49

3-n-Butylamino-4-phenoxy-5-sulphamyl-benzamide

To a solution of 3-butylamino-4-phenoxy-5-sulphamyl-benzoic acid (1 g) in dry acetone (10 ml), triethylamine (0.278 g) was added. Methanesulphonyl chloride (0.315 g) in dry acetone (5 ml) was added to the reaction mixture, while stirring. The agitation was continued for 1.5 hours at 20° C. The resulting solution of the mixed anhydride was added dropwise to aqueous ammonia (30 ml containing 7 g of ammonia), while stirring. Then excess of ammonia and acetone were removed by evaporation under reduced pressure. The pH of the reaction mixture was adjusted to 7.5 by means of 4N hydrochloric acid, and the precipitated 3-butylamino-4-phenoxy-5-sulphamyl-benzamide was isolated by filtration and recrystallized several times from aqueous ethanol. After drying in vacuo at 115° C, the compound was obtained with a melting point of 223°–224° C.

EXAMPLE 50

3-Benzylamino-4-phenylthio-5-sulphamyl-benzoic acid

A suspension of 3-amino-4-phenylthio-5-sulphamyl-benzoic acid (4.05 g) in water (100 ml) was adjusted to pH 7.5 by addition of 1N lithium hydroxide. Benzyl bromide (2.2 g) was added and, under stirring, the pH was kept at 7.5 by automatic titration with lithium hydroxide. After the base consumption had become negligible, the pH was adjusted to 2.5 by addition of dilute hydrochloric acid. The precipitated 3-benzylamino-4-phenylthio-5-sulphamyl-benzoic acid was collected and recrystallized from ethanol, whereafter the compound was obtained with a melting point of 224°–225° C.

3-Benzylamino-4-phenoxy-5-sulphamyl-benzoic acid

By substituting 3-amino-4-phenoxy-5-sulphamyl-benzoic acid (3.8 g) for the 3-amino-4-phenylthio-5-sulphamyl-benzoic acid above, 3-benzylamino-4-phenoxy-5-sulphamyl-benzoic acid was obtained, after recrystallization from dilute ethanol, with a melting point of 264°–265° C.

EXAMPLE 51

3-n-Butylamino-4-phenylsulphinyl-5-sulphamyl-benzoic acid

A. 3-n-Butylamino--4-phenylthio-5-sulphamyl-benzoic acid and its sodium salt

To a suspension of 3-amino-4-phenylthio-5-sulphamyl-benzoic acid (10 g) in n-butanol (200 ml), concentrated sulphuric acid (2 ml) was added while stirring. The reaction mixture was heated under reflux under conditions at which the water formed during the reaction was separated. When the NMR-spectrum of a sample of the reaction mixture diluted with n-butanol, showed at the two doublets of the aromatic protons of the ring carrying the sulphamyl group that more than 90 per cent of the formed butyl-3-amino-4-phenylthio-5-sulphamyl-benzoate intermediate was converted into the corresponding 3-n-butylaminobenzoate, which caused a frequence shift to a higher field, 2N sodium hydroxide (200 ml) was added, and the boiling was continued for 45 minutes. After this saponification, the reaction mixture was neutralized to a pH of 8 by the addition of concentrated hydrochloric acid. After cooling, the sodium salt of 3-n-butylamino-4-phenylthio-5-sulphamyl-benzoic acid precipitated. It was filtered off and recrystallized from water (100 ml). The sodium salt, which crystallized with 3 molecules of water of crystallization, was then dissolved in boiling water (200ml). 1N hydrochloric acid was added until the pH was 2.5, and, after cooling, the precipitated 3-n-butylamino-4-phenylthio-5-sulphamyl-benzoic acid was collected by filtration. After recrystallization from aqueous ethanol and drying, the pure compound was obtained with a melting point of 203°–204° C.

B. 3-n-Butylamino-4-phenylsulphinyl-5-sulphamyl-benzoic acid

To a suspension of 3-n-butylamino-4-phenylthio-5-sulphamyl-benzoic acid (0.5 g) in acetic acid (5 ml), perhydrol (2.5 ml of 30% hydrogen peroxide in water) was added while stirring. The reaction mixture was stirred for an additional 24 hours at 30° C, after which the 3-n-butylamino-4-phenylsulphinyl-5-sulphamyl-benzoic acid was collected by suction and washed with aqueous acetic acid. After recrystallization from aqueous ethanol, the compound was obtained with a melting point of 203°–204° C (decomp.).

EXAMPLE 52

4-Anilino-3-benzylamino-5-sulphamyl-benzoic acid

A. Ethyl-4-anilino-3-benzylamino-5-sulphamyl-benzoate

A mixture of 3 -amino-4-anilino-5-sulphamyl-benzoic acid (2 g), benzyl bromide (3 g), and ethanol (50 ml 99.9%) was refluxed for 8 hours. After cooling, the ethyl-4-anilino-3-benzylamino-5-sulphamyl-benzoate crystallized and was collected by suction. After recrystallization from ethanol the melting point was 160°–161° C.

B. 4-Anilino-3-benzylamino-5-sulphamyl-benzoic acid

A solution of ethyl-4-anilino-3-benzylamino-5-sulphamyl-benzoate (1 g) in 1N sodium hydroxide (15 ml) was heated on a steam bath for 1 hour. After cooling, the 4-anilino-3-benzylamino-5-sulphamyl-benzoic acid was precipitated by addition of acetic acid, collected and recrystallized from 60% ethanol in water. The melting point was 248°–249° C.

EXAMPLE 53

4-Anilino-3-benzylamino-5-phenylsulphamyl-benzoic acid

A. Ethyl-4-anilino-3-benzylamino-5-phenylsulphamy-benzoate

By replacing, in Example 52 A, 3-amino-4-anilino-5-sulphamyl-benzoic acid (2 g) by 3-amino-4-anilino-5-phenylsulphamyl-benzoic acid (4.4 g) and increasing the amount of benzyl bromide to 3.9 g, ethyl-4-anilino-3-benzylamino-5-phenylsulphamyl-benzoate was obtained with a melting point of 166°–167° C.

B. 4-Anilino-3-benzylamino-5-phenylsulphamyl-benzoic acid

A solution of ethyl-4-anilino-3-benzylamino-5-phenylsulphamyl-benzoate (3 g) in 1N sodium hydroxide (30 ml) was heated on a steam bath for 1 hour. The 4-anilino-3-benzylamino-5-phenylsulphamyl-benzoic acid was precipitated by addition of 4N hydrochloric acid until pH 2, and recrystallized from acetone-water and 80% ethanol in water; the melting point was 243° C.

EXAMPLE 54

3-Benzylamino-4-phenylsulphinyl-5-sulphamyl-benzoic acid

To a suspension of 3-benzylamino-4-phenylthio-5-sulphamyl-benzoic acid (0.8 g) in acetic acid (20 ml), perhydrol (1.5 ml of 30% hydrogen peroxide in water) was added while stirring. The reaction mixture was stirred for an additional 75 hours at room temperature, after which the 3-benzylamino-4-phenylsulphinyl-5-sulphamyl-benzoic acid was collected by filtration and washed with acetic acid. After recrystallization from aqueous methanol and drying, the acid had a melting point of 234° C.

EXAMPLE 55

3-Benzylamino-4-n-butylsulphinyl-5-sulphamyl-benzoic acid

A mixture of 3-amino-4-n-butylsulphinyl-5-sulphamyl-benzoic acid (2 g), benzyl bromide (3.5 g), and dry ethanol (20 ml) was refluxed for 16 hours. The reaction mixture was evaporated in vacuo. The residue, containing the ethyl-3-benzylamino-4-n-butylsulphinyl-5-sulphamyl-benzoate, was saponified by addition of 1N sodium hydroxide (30 ml) and standing for 16 hours at room temperature. After extraction with diethyl ether, the aqueous layer was adjusted to a pH of 7.4 by addition of 4N hydrochloric acid and the sodium salt of 3-benzylamino-4-n-butylsulphinyl-5-sulphamyl-benzoic acid was precipitated by addition of sodium chloride (5 g). The sodium salt was isolated and recrystallized from a little amount of water. The salt was dissolved in aqueous ethanol (25% ethanol in water) and the 3-benzylamino-4-n-butylsulphinyl-5-sulphamyl-benzoic acid was precipitated by addition of 4N hydrochloric acid until a pH of 3. After recrystallization from aqueous ethanol and drying in vacuo, the compound was obtained as a monohydrate with a melting point of 182° C (decomp.).

EXAMPLE 56

3-(3,4-Methylenedioxybenzylamino)-4-phenoxy-5-sulphamylbenzoic acid

To a suspension of 3-amino-4-phenoxy-5-sulphamyl-benzoic acid (1.54 g) in acetic acid (30 ml), piperonal (0.75 g) was added. After the addition of platinum oxide (25 mg) and a catalytic amount of p-toluenesulphonic acid, the reaction mixture was hydrogenated at room temperature and 1.1 atmospheres hydrogen pressure until the hydrogen uptake had become negligible. Then the reaction mixture was filtered by suction. The filter cake was suspended in water (100 ml), and the pH was adjusted to 8.5 by addition of lithium hydroxide. After the catalyst had been removed from the resulting solution, the 3-(3,4-methylenedioxybenzylamino)-4-phenoxy-5-sulphamyl-benzoic acid was precipitated from the filtrate by addition of 4N hydrochloric acid until the pH was 3. After recrystallization from methanol, the melting point was 229°–230° C.

3-(Methoxy-, methyl-, or chloro-benzylamino)-4-phenoxy-5-sulphamyl-benzoic acids By substituting methyl-, methoxy-, or chloro-benzaldehyde (0.005 mole) for the piperonal above and recrystallization from aqueous ethanol, the corresponding benzoic acids were obtained.

EXAMPLE 57

3-n-Hexylamino-4-phenoxy-5-sulphamyl-benzoic acid, and its sodium salt

A. n-Hexyl-3-n-hexylamino-4-phenoxy-5-sulphamyl-benzoate

A mixture of 3-amino-4-phenoxy-5-sulphamyl-benzoic acid (4.62 g), 1-bromo-n-hexane (5 g), methanesulphonic acid (0.05 ml), and n-hexanol (40 ml) was refluxed for 60 hours. After cooling, the precipitated n-hexyl-3-n-hexylamino-4-phenoxy-5-sulphamyl-benzoate was collected and recrystallized from hexanol. The melting point was 137°–138° C.

B. 3-n-Hexylamino-4-phenoxy-5-sylphamyl-benzoic acid, and its sodium salt n-Hexyl-3-n-hexylamino-4-phenoxy-5-sulphamyl-benzoate (2 g) was dissolved in 1N sodium hydroxide (30 ml) and heated on a steam bath for 1 hour. Then the reaction mixture was adjusted to a pH of 8 by addition of 4N hydrochloric acid. After cooling, the sodium salt of 3-n-hexylamino-4-phenoxy-5-sulphamyl-benzoic acid was collected by suction and dried. The sodium salt was dissolved in hot water (100 ml), and the acid was precipitated by the addition of 4N hydrochoric acid until the pH was 2.5. After cooling, the acid was collected and recrystallized from aqueous ethanol. The melting point was 221°–223° C.

EXAMPLE 58

3-Allylamino-4-phenoxy-5-sulphamyl-benzoic acid

A. Ethyl-3-allylamino-4-phenoxy-5-sulphamyl-benzoate

A mixture of 3-amino-4-phenoxy-5-sulphamyl-benzoic acid (3.08 g), allyl bromide (7.25 g), and dry ethanol was refluxed for 24 hours. After cooling, the precipitated ethyl-3-allylamino-4-phenoxy-5-sulphamyl-benzoate was filtered off and recrystallized from ethanol. The melting point of the ester was 153°–154° C.

B. 3-Allylamino-4-phenoxy-5-sulphamyl-benzoic acid

Ethyl-3-allylamino-4-phenoxy-5-sulphamyl-benzoate (1 g) was dissolved in 1N sodium hydroxide (15 ml) and left standing at room temperature for 24 hours. Then water (5 ml) was added, and the pH was adjusted to 3 by the addition of 4N hydrochloric acid. The precipitated 3-allylamino-4-phenoxy-5-sulphamyl-benzoic acid was collected and dried. The melting point was 233°–225° C.

EXAMPLE 59

4-Phenoxy-3-propargylamino-5-sulphamyl-benzoic acid

A. Ethyl-4-phenoxy-3-propargylamino-5-sulphamyl-benzoate

By substituting propargyl bromide (4.8 g) for the allyl bromide of Example 58 A and extending the reaction time to 48 hours, ethyl-4-phenoxy-3-propargylamino-5-sulphamyl-benzoate was obtained with a melting point of 189°–190° C.

B. 4-Phenoxy-3-propargylamino-5-sulphamyl-benzoic acid

By substituting ethyl-4-phenoxy-3-propargylamino-5-sulphamyl-benzoate for the ethyl-3-allylamino-4-phenoxy-5-sulphamyl-benzoate of Example 58 B and by recrystallizing from dilute ethanol, 4-phenoxy-3-propargylamino-5sulphamyl-benzoic acid was obtained with a melting point of 222°–223° C.

EXAMPLE 60

4-Phenoxy-3-n-propylamino-5-sulphamyl-benzoic acid

A. Ethyl-4-phenoxy-3-n-propylamino-5sulphamyl-benzoate

A solution of ethyl-3-allylamino-4-phenoxy-5-sulphamyl-benzoate (1.65 g) in ethanol (150 ml) was hydrogenated at room temperature and 1.1. atmospheres hydrogen pressure after the addition of a palladium-on-carbon catalyst (0.6 g catalyst containing 10% Pd). After the hydrogen uptake had become negligible, the catalyst was removed by filtration, and the filtrate was evaporated in vacuo. The residue was recrystallized twice from aqueous ethanol, resulting in ethyl-4-phenoxy-3-n-propylamino-5-sulphamyl-benzoate with a melting point of 150°–151° C.

B. 4-Phenoxy-3-n-propylamino-5-sulphamyl-benzoic acid

Ethyl-4-phenoxy-3-n-propylamino-5-sulphamyl-benzoate (1 g) was dissolved in 1N sodium hydroxide (15 ml), and heated on a steam bath for 1 hour. After cooling, the 4-phenoxy-3-n-propylamino-5-sulphamyl-benzoic acid was precipitated by addition of 4N hydrochloric acid until the pH was 2.5; the melting point was 223°–224° C.

EXAMPLE 61

3-Ethylamino-4-phenoxy-5-sulphamyl-benzoic acid

A mixture of 3-amino-4-phenoxy-5-sulphamyl-benzoic acid (3.08 g), ethyl iodide (20 ml), and ethanol (20 ml) was refluxed for 6 days. After cooling, the reaction mixture was evaporated to dryness, and the residue was washed with a little ethanol followed by diethyl ether. The ethyl 3-ethylamino-4-phenoxy-5-sulphamyl-benzoate obtained was dissolved in 1N sodium hydroxide (35 ml) and heated on a steam bath for 30 minutes. After cooling, the reaction mixture was adjusted to pH 2.5 by addition of 4N hydrochloric acid, and the precipitated 3-ethylamino-4-phenoxy-5-sulphamyl-benzoic acid was isolated by filtration. After recrystallization from ethanol and drying in vacuo at 115° C, the compound was obtained with a melting point of 236°–237° C.

EXAMPLE 62

3-n-Pentylamino-4-phenoxy-5-sulphamyl-benzoic acid

A. n-Pentyl-3-n-pentylamino-4-phenoxy-5-sulphamyl-benzoate

A mixture of 3-amino-4-phenoxy-5-sulphamyl-benzoic acid (6 g), n-pentanol (60 ml), and conc. sulphuric acid (0.5 ml) was refluxed for 24 hours. After cooling, the precipitated n-pentyl 3-pentylamino-4-phenoxy-5-sulphamyl-benzoate was isolated by filtration and recrystallized from n-pentanol. After drying in vacuo, the compound was obtained with a melting point of 138°–139° C.

B. 3-n-Pentylamino-4-phenoxy-5-sulphamyl-benzoic acid

A mixture of n-pentyl 3-n-pentylamino-4-phenoxy-5-sulphamyl-benzoate (4.5 g) and 1N sodium hydroxide (70 ml) was heated on a steam bath for 1 hour. After cooling, the reaction mixture was adjusted to a pH of 2.5 by addition of 4N hydrochloric acid. The precipitated 3-n-pentylamino-4-phenoxy-5-sulphamyl-benzoic acid was isolated by filtration and recrystallized from aqueous ethanol. After drying in vacuo, the compound was obtained with a melting point of 223°–224° C.

EXAMPLE 63

3-Benzylamino-4-(4benzyloxyphenoxy)-5-sulphamyl-benzoic acid

A. Ethyl 3-benzylamino-4-(4-benzyloxyphenoxy)-5-sulphamyl-benzoate

A mixture of 3-amino-4-(4-benzyloxyphenoxy)-5-sulphamyl-benzoic acid (4 g), benzyl bromide (4.1 g), and ethanol (60 ml) was refluxed for 4 hours. After cooling, the precipitated ethyl 3-benzylamino-4-(4-benzyloxyphenoxy)-5-sulphamyl-benzoate was isolated by filtration and recrystallized from ethanol. The compound was obtained with a melting point of 166° C.

B. 3-Benzylamino-4-(4-benzyloxyphenoxy)-5-sulphamylbenzoic acid

A solution of ethyl 3-benzylamino-4-(4-benzyloxyphenoxy)-5-sulphamyl-benzoate (2 g) in 1N sodium hydroxide (45 ml) was left standing at room temperature for 40 hours. Then the reaction mixture was adjusted to a pH of 2.5 by addition of 4N hydrochloric acid. The precipitated 3-benzylamino-4-(4-benzyloxyphenoxy)-5-sulphamyl-benzoic acid was isolated by filtration and recrystallized from aqueous ethanol. After drying, the compound was obtained with a melting point of 249°–251° C.

EXAMPLE 64

3-Benzylamino-4-(4-hydroxyphenoxy)-5-sulphamyl-benzoic acid

A suspension of 3-benzylamino-4-(4-benzyloxyphenoxy)-5-sulphamyl-benzoic acid (0.5 g) in water (5 ml) was adjusted to a pH of 11 by addition of 1N sodium hydroxide. The resulting solution was hydrogenated at room temperature and 1.1 atmospheres hydrogen pressue after addition of Pd-on-carbon powder catalyst (0.025 g catalyst containing 10% of Pd). After the hydrogen uptake had become negligible, the catalyst was removed by filtration, and from the filtrate the 3-benzylamino-4-(4-hydroxyphenoxy)-5-sulphamyl-benzoic acid was precipitated by addition of 4N hydrochloric acid until a pH of 2. After isolation by filtration and recrystallization from aqueous ethanol, the compound was obtained with a melting point of 276°–277° C (decomp.).

EXAMPLE 65

3-Furfurylamino-4-phenoxy-5-sulphamyl-benzoic acid and its sodium salt

A. Sodium salt of 3-amino-4-phenoxy-5-sulphamyl-benzoic acid

A suspension of 3-amino-4-phenoxy-5-sulphamyl-benzoic acid (10 g) in water (25 ml) was adjusted to a pH of 8 by addition of 1N sodium hydroxide at 80° C. After cooling, the precipitated sodium salt was collected by suction and dried in vacuo at 115° C.

B. Sodium salt of 3-furfurylamino-4-phenoxy-5-sulphamyl-benzoic acid

A mixture of the sodium salt of 3-amino-4-phenoxy-5-sulphamyl-benzoic acid (5 g), furfural (2.2 g), and methanol (75 ml) was refluxed for 5 hours. Then the reaction mixture was cooled to 0° C and sodium borohydride, $NaBH_4$, (2.2 g) was added in portions during 1 hour, while stirring and keeping the temperature at 0°–5° C. After standing for 16 hours, the solvent was distilled off in vacuo, and the residue was dissolved in water (45 ml). The solution was adjusted to a pH of 7.5 by addition of 4N hydrochloric acid and cooled. The precipitated sodium salt of 3-furfurylamino-4-phenoxy-5-sulphamyl-benzoic acid was collected by suction, recrystallized from water, and dried.

C. 3-Furfurylamino-4-phenoxy-5-sulphamyl-benzoic acid

The sodium salt of 3-furfurylamino-4-phenoxy-5-sulphamyl-benzoic acid (1 g) was dissolved in water (50 ml) at 50°C and acetic acid (1 ml) was added dropwise, while stirring. After cooling, the precipitated acid was collected by suction and recrystallized from aqueous ethanol. The melting point was 219°–220° C.

EXAMPLE 66

3,4-Dibenzylamino-5-sulphamyl-benzoic acid, and its sodium salt

A suspension of 3-amino-4-benzylamino-5-sulphamyl-benzoic acid (1 g) in water (20 ml) was adjusted to a pH of 7.5 by addition of 1N sodium hydroxide. To the solution benzyl bromide (0.54 g) was added and, while stirring, the pH was kept at 7.5 by automatic titration with sodium hydroxide. After the base consumption had become negligible, the precipitated sodium salt of 3,4-dibenzylamino-5-sulphamyl-benzoic acid was collected by suction and washed with a little water. The sodium salt was dissolved in aqueous ethanol (62 ml containing 25% of ethanol), and the acid was precipitated by addition of acetic acid (2 ml). The acid was collected by suction and dried. The melting point was 205° C.

EXAMPLE 67

3-Benzylamino-4-(β-phenylethylamino)-5-sulphamyl-benzoic acid

A mixture of 3-amino-4-(β-phenylethylamino)-5-sulphamyl-benzoic acid (3.35 g), benzyl bromide (5.3 g), and anhydrous ethanol (30 ml) was refluxed for 48 hours. After cooling, the precipitated ethyl ester was collected by suction, recrystallized from ethanol and saponified by heating in 1N sodium hydroxide (30 ml) for 1 hour. The 3-benzylamino-4-(β-phenylethylamino)-5-sulphamyl-benzoic acid was precipitated at room temperature by addition of 4N hydrochloric acid until the pH was 2.5. After recrystallization from aqueous ethanol, the compound was obtained with a melting point of 203° C.

EXAMPLE 68

3-Benzylamino-4-piperidino-5-sulphamyl-benzoic acid

A mixture of 3-amino-4-piperidino-5-sulphamyl-benzoic acid (2.5 g), benzyl bromide (1.4 g), and dry ethanol (30 ml) was refluxed for 3 days. The reaction mixture was evaporated in vacuo, and the residue was washed with petroleum ether. The crude ethyl 3-benzylamino-4-piperidino-5-sulphamyl-benzoate obtained was saponified by addition of 1N sodium hydroxide and heated on a steam bath for 1 hour. After cooling and adjusting the pH to 4 by means of a 4N hydrochloric acid, 3-benzylamino-4-piperidino-5-sulphamyl-benzoic acid precipitated. After collecting and recrystallizing from aqueous ethanol, the compound was obtained as a hemi-hydrate with a melting point of 195° C.

Example 69

3-Benzylamino-4-isopropylamino-5-sulphamyl-benzoic acid

A mixture of 3-amino-4-isopropylamino-5-sulphamyl-benzoic acid (2.62 g), benzyl bromide (4.28 g), and anhydrous ethanol (25 ml) was refluxed for 24 hours. The reaction mixture was evaporated in vacuo. 1N sodium hydroxide (30 ml) was added, and the mixture was heated on a steam bath for 1 hour. After cooling and extracting with diethyl ether, the aqueous layer was adjusted to a pH of 3 by addition of a 4N hydrochloric acid. The precipitated 3-benzylamino-4-isopropylamino-5-sulphamyl-benzoic acid was collected by suction and recrystalized from aqueous ethanol. The melting point was 233°–234° C.

Example 70

3-Benzylamino-4-(2-methyl-6-pyridylamino)-5-sulphamyl-benzoic acid

A suspension of 3-amino-4-(2-methyl-6-pyridylamino)-5-sulphamyl-benzoic acid (0.5 g) in water (25 ml) was adjusted to a pH of 8 by addition of 1N lithium hydroxide. To the resulting solution, benzyl bromide (0.2 g) was added while, under stirring, the pH was kept at 8 by automatic titration with 1N lithium hydroxide. After the base consumption had become negligible, the crude 3-benzylamino-4-(2-methyl-6-pyridylamino)-5-sulphamyl-benzoic acid was precipitated from the reaction mixture by adjusting the pH to 5 by means of 1N hydrochloric acid. The compound was collected by suction, recrystallized from aqueous ethanol, and dried. The melting point of the compound was 168°–170° C.

Example 71

Ethyl 3-benzylamino-5-sulphamyl-4-(m-trifluoromethylphenoxy)-benzoate

A mixture of 3-amino-5-sulphamyl-4-(m-trifluoromethylphenoxy)-benzoic acid (1.82 g), benzyl bromide (2 g), and anhydrous ethanol (15 ml) was refluxed for 7 hours. The solution was cooled, and the precipitated ethyl 3-benzylamino-5-sulphamyl-4-(m-trifluoromethylphenoxy)benzoate was collected by suctin. After recrystallizatin from ethanol, the melting point was 166°–168° C.

Ethyl 3-benzylamino-4-(p-methoxyanilino)-5-sulphamyl-benzoate

By substituting 3-amino-4-(p-methoxyanilino)-5-sulphamyl-benzoic acid (1.69 g) for the 3-amino-5-sulphamyl-4-(m-trifluoromethylphenoxy)-benzoic acid and extendng the heating time to 20 hours, the above compound was obtained with a melting point of 145° C.

Ethyl 3-benzylamino-4-(m-methoxyanilino)-5-sulphamyl-benzoate

By substituting 3amino-4-(m-methoxyanilino)-5-sulphamyl-benzoic acid (1.69 g) for the 3-amino-5-sulphamyl-4-(m-trifluoromethylphenoxy)-benzoic acid and extending the heating time to 20 hours, the above compound was obtained with a melting point of 149°–152° C.

Ethyl 3-benzylamino-4-(p-methoxyphenoxy)-5-sulphamyl-benzoate

By substituting 3-amino-4-(p-methoxyphenoxy)-5-sulphamyl-benzoic acid (1.69 g) for the 3-amino-5-sulphamyl-4-(m-trifluoromethylphenoxy)-benzoic acid, the above compound was obtained as a precipitate during the heating time. After collection by suction and recrystallizing from acetone, the compound had a melting point of 189°–190° C.

Ethyl 3-benzylamino-4-cyclohexylamino-5-sulphamyl-benzoate

By substituting 3-amino-4-cyclohexylamino-5-sulphamyl-benzoic acid (1.5 g) for the 3-amino-5-sulphamyl-4-(m-trifluoromethylphenoxy)-benzoic acid and adding water (13 ml) to the cooled reaction mixture, the above compound was obtained with a melting point of 176°–177° C.

Ethyl 3-benzylamino-5-sulphamyl-4-(m-trifluoromethylanilino)-benzoate

By substituting 3-amino-5-sulphamyl-4-(m-trifluoromethylanilino)-benzoic acid (1.8 g) for the 3-amino-5-sulphamyl-4-(m-trifluoromethylphenoxy)-benzoic acid and increasing the amount of ethanol to 50 ml, the above compound was obtained with a melting point of 189°–190° C.

Ethyl 3-benzylamino-4-(β-naphthylamino)-5-sulphamyl-benzoate

By substituting 3-amino-4-(β-naphthylamino)-5-sulphamyl-benzoic acid (1.8 g) for the 3-amino-5-sulphamyl-4-(m-trifluoromethylphenoxy)-benzoic acid and increasing the amount of ethanol to 25 ml, the above compound was obtained with a melting point of 199°–201° C.

Example 72

Ethyl 3-benzylamino-5-sulphamyl-4-(m-toluidino)-benzoate

A mixture of 3-amino-5-sulphamyl-4-(m-toluidino)-benzoic acid (1.5 g), benzyl bromide (2.5 g), and anhydrous ethanol (50 ml) was heated under reflux for 10 hours. The resulting solution was cooled, and the precipated ethyl 3-benzylamino-5-sulphamyl-4-(m-toluidino)-benzoate was collected by suction. After recrystallization from ethanol, the compound had a melting point of 169°–170° C.

Ethyl 3-benzylamino-5-sulphamyl-4-(p-toluidino)-benzoate

By substituting 3-amino-5-sulphamyl-4-(p-toluidino)-benzoic acid for the 3-amino-5-sulphamyl-4-(m-toluidino)-benzoic acid, the above compound was obtained with a melting point of 159°–160° C.

Ethyl 3-benzylamino-4-(p-chloroanilino)-5-sulphamyl-benzoate

By substituting 3-amino-4-(p-chloroanilino)-5-sulphamyl-benzoic acid (2 g) for the 3-amino-5-sulphamyl-4-(m-toluidino)-benzoic acid, the above compound was obtained with a melting point of 187° C.

Ethyl 3-benzylamino-4-(2,4-dimethylanilino)-5-sulphamyl-benzoate

By substituting 3-amino-4-(2,4-dimethylanilino)-5-sulphamyl-benzoic acid (2 g) for the 3-amino-5-sulphamyl-4-(m-toluidino)-benzoic acid, the above compound was obtained with a melting point of 167°–168° C.

Example 73

Ethyl 3-benzylamino-4-n-(butylthio)-5-sulphamyl-benzoate

A mixture of 3-amino-4-(n-butylthio)-5-sulphamyl-benzoic acid (1.5 g), benzyl bromide (2.1 g), and anhydrous ethanol, (20 ml) was refluxed for 24 hours. After the first 7 hours of refluxing, benzyl bromide (0.7 g) was added. After cooling, the precipitated ethyl 3-benzylamino-4-(n-butylthio)-5-sulphamyl-benzoate was collected and recrystallized from ethanol, after which the compound was obtained with a melting point of 151°–157° C.

Ethyl 3-benzylamino-4-(p-carbethoxyanilino)-5-sulphamyl-benzoate

By substituting 3-amino-4-(p-carboxyanilino)-5-sulphamyl-benzoic acid (1.7 g) for the 3-amino-4-(n-butylthio)-5-sulphamyl-benzoic acid, the above compound was obtained with a melting point of 161° C.

Example 74

Ethyl 3-benzylamino-4-morpholino-5-sulphamyl-benzoate

A mixture of 3-amino-4-morpholino-5-sulphamyl-benzoic acid (3 g), benzyl bromide (4 g), and anhydrous ethanol (45 ml) was refluxed. After 24 hours and again after 48 hours a solution of benzyl bromide (1.5 g) in anhydrous ethanol (5 ml) was added during 4 hours. After the second addition, the refluxing was continued for 24 hours. The reaction mixture was cooled, and the precipitated ethyl 3-benzylamino-4-morpholino-5-sulphamyl-benzoate was collected by suction and recrystallized from ethanol, after which the compound was obtained with a melting point of 185°–186° C.

Ethyl 3-benzylamino-5-sulphamyl-4-(o-tolylthio)-benzoate

By substituting 3-amino-5-sulphamyl-4-(o-tolylthio) benzoic acid for the 3-amino-4-morpholino-5-sulphamyl benzoic acid, the above compound was obtained with a melting point of 166°–167° C.

Example 75

Ethyl 3-benzylamino-5-sulphamyl-4-($\beta,\beta,\beta$-trifluoroethoxy) benzoate A mixture of 3-amino-5-sulphamyl-4-($\beta,\beta,\beta$-trilfuoroethoxy)-benzoic acid (0.6 g), benzyl bromide (1.2 g), and dry ethanol (8 ml) was refluxed for 5 hours. After cooling, the precipitated ethyl 3-benzylamino-5-sulphamyl-4-($\beta,\beta,\beta$-trifluoroethoxy)-benzoate was collected by suction and recrystallized from dry ethanol. After drying, the compound had a melting point of 163°–165° C.

Example 76

4-Substituted 3-benzylamino-5-sulphamyl-benzoic acids by saponification of the corresponding ethyl esters General procedure:

The corresponding ethyl ester (2g), prepared as in Examples 71 to 75, was dissolved in 1N sodium hydroxide (30 ml) and heated on a steam bath for 1 hour. After cooling, the acid was precipitated by addition of 4N hydrochloric acid, until the pH was 2.5, collected by suction, recrystallized from aqueous ethanol, and dried at 115° C in vacuo.

The following acids were obtained:

3-Benzylamino-5-sulphamyl-4-(m-toluidino)-benzoic acid with a melting point of 226°–227° C.

3-Benzylamino-5-sulphamyl-4-(p-toluidino)-benzoic acid with a melting point of 217°–218° C.

3-Benzylamino-4-(p-methoxyanilino)-5-sulphamyl-benzoic acid with a melting point of 207°–208° C.

3-Benzylamino-5-sulphamyl-4-(m-trifluoromethylanilino)-benzoic acid with a melting point of 227°–228° C after recrystallization from isopropanol.

3-Benzylamino-4-(p-chloroanilino)-5-sulphamyl-benzoic acid with a melting point of 245°–246° C.

3-Benzylamino-4-(2,4-dimethylanilino)-5-sulphamyl-benzoic acid with a melting point of 245°–246° C 3-Benzylamino-4-(p-carboxylanilino)-5-sulphamyl-benzoic acid prepared from ethyl 3-benzylamino-4-(p-carbethoxyanilino)-5-sulphamyl-benzoic acid and precipitated at a pH of 1.5 with a melting point higher than 300° C and containing ½ molecule of water of crystallization.

3-Benzylamino-5-sulphamyl-4-(o-tolylthio)-benzoic acid with a melting point of 227°–228°C.

3-Benzylamino-4-(p-methoxyphenoxy)-5-sulphamyl-benzoic acid with a melting point of 230°–232° C.

3-Benzylamino-5-sulphamyl-4-(m-trifluoromethyl-phenoxy)-benzoic acid with a melting point of 220°–222° C.

3-Benzylamino-4-($\beta$-naphthylamino)-5-sulphamyl-benzoic acid with a melting point of 261°–263° C.

3-Benzylamino-4-cyclohexylamino-5-sulphamyl-benzoic acid with a melting point of 249°–250° C.

3-Benzylamino-4-morpholino-5-sulphamyl-benzoic acid with a melting point of 237° C.

3-Benzylamino-4-(n-butylthio)-5-sulphamyl-benzoic acid with a melting point of 210°–211° C.

3-Benzylamino-5-sulphamyl-4-($\beta,\beta,\beta$-trifluoroethoxy)-benzoic acid with a melting point of 230°–232° C.

Example 77

4-Anilino-3-butylamino-5-sulphamyl-benzoic acid

A mixture of 3-amino-4-anilino-5-sulphamyl-benzoic acid (4 g), n-butanol (50 ml), and conc. $H_2SO_4$ (0.4 ml) was boiled under reflux with water separator for 5 days. The resulting solution of butyl 4-anilino-3-butylamino-5-sulphamyl-benzoate was saponified by addition of 2N sodium hydroxide and boiling under reflux for 45 minutes. After neutralization with 4N hydrochloric acid, the reaction mixture was evaporated in vacuo. The residue was dissolved in hot water (50 ml), and the 4-anilino-3-butylamino-5-sulphamyl-benzoic acid was precipitated by addition of 4N hdyrochloric acid to pH 3. The crude acid was dissolved in diethyl ether (50 ml), and undissolved impurities were filtered off. The etherial solution was evaporated to dryness, and the residue was recrystallized from acetone-water and aqueous ethanol, after which the compound was obtained with a melting point of 230°–231° C.

EXAMPLE 78

3-Benzylamino-4-butylamino-5-sulphamyl-benzoic acid

A. 4-Butylamino-3-nitro-5-sulphamyl-benzoic acid

A mixture of 4-chloro-3-nitro-5-sulphamyl-benzoic acid (8.4 g), n-butylamine (8.7 g), and water (25 ml) was stirred at 90° C for 1.5 hours. After cooling, the pH was adjusted to pH 2, and the precipitated 4-butylamino-3-nitro-5-sulphamyl-benzoic acid was collected by filtration. After several recrystallizations from aqueous methanol the melting point was 192.5° C.

B. 3-Amino-4-butylamino-5-sulphamyl-benzoic acid

A suspension of 4-butylamino-3-nitro-5-sulphamyl-benzoic acid (8.6 g) in water (175 ml) was adjusted to pH 9.5 by addition of 2N sodium hydroxide. The resulting solution was hydrogenated after additon of Pd-on-carbon catalyst (0.5 g catalyst containing 10% Pd). After the hydrogen uptake had become negligible, the catalyst was removed by filtration, and the 3-amino-4-butylamino-5-sulphamyl-benzoic acid was precipitated from the filtrate by addition of 4N hyrochloric acid until pH 3. After recrystallization from aqueous methanol the melting point was 211°–211.5° C.

C. 3-Benzylamino-4-butylamino-5-sulphamyl-benzoic acid

A suspension of 3-amino-4 -butylamino-5-sulphamyl-benzoic acid (6.5 g) in water (30 ml) was adjusted to pH 7.5 by addition of 1N sodium hydroxide. Benzyl bromide (3.87 g) was added and, under stirring, the pH was kept at pH 7.5 by automatic titration with 1N sodium hydroxide. After the base consumption had become negligible, the pH was adjusted to 3 by addition of diluted hydrochloric acid. The precipitated 3-benzylamino-4-butylamino-5-sulphamyl-benzoic acid was collected and recrystallized several times from aqueous methanol, after which the compound was obtained with a melting point of 198.5°–199° C.

Example 79

5-Acetylsulphamyl-3-benzylamino-4-phenoxy-benzoic acid

A mixture of 3-amino-5-acetylsulphamyl-4-phenoxy-benzoic acid (1 g), benzaldehyde (0.3 g), and acetic acid (40 ml) was heated on a steam bath for 2 hours. After cooling to room temperature, platinum oxide catalyst (0.035 mg) was added, and the reaction mixture was hydrogenated at room temperature and at 1.1 atmospheres hydrogen pressure. After the hydrogen uptake had become negligible, the catalyst was removed by filtration, and the filtrate evaporated in vacuo. After several recrystallizations of the residue from aqueous ethanol, and after drying in vacuo at 76° C, the compound was obtained with a melting point of 241°–243° C. The compound crystallized as a hemihydrate.

Example 80

3-Benzylamino-4-phenoxy-5-sulphamyl-benzoic acid

A mixture of 5-acetylsulphamyl-3-benzylamino-4-phenoxy-benzoic acid (1 g), ethanol (20 ml), and 4N hydrochloric acid (5ml) was refluxed for 2.5 hours. Then 2N sodium hydroxide (15 ml) was added, and the reaction mixture was heated on a steam bath for 30 minutes. After cooling, the pH was adjusted to 2.5 by addition of 4N hydrochloric acid, and the precipitated 3-benzylamino-4-phenoxy-5-sulphamyl-benzoic acid was isolated by filtation. After recrystallization from aqueous ethanol and drying, the compound was obtained with a melting point of 264°–265° C.

Example 81

3-Benzylamino-5-methylsulphamyl-4-phenoxy-benzoic acid

A. Ethyl 3-benzylamino-5-methylsulphamyl-4-phenoxy-benzoate

A mixture of 3-amino-5-methylsulphamyl-4-phenoxy-benzoic acid (1 g), benzyl bromide (1.25 g), and dry ethanol (15 ml) was refluxed for 9 hours. After 3 hours and after 6 hours more benzyl bromide (0.6 g) was added. After cooling, the precipitated ethyl 3-benzylamino -5-methylsulphamyl-4-phenoxy-benzoate was collected by suction, recrystallized from ethanol, and dried in vacuo. The melting point of the compound was 162.5° C.

B. 3-Benzylamino-5-methylsulphamyl-4-phenoxy-benzoic acid

Ethyl 3-benzylamino-5-methylsulphamyl-4-phenoxy-benzoate (0.5 g) was dissolved in 1N sodium hydroxide (8 ml) and heated on a steam bath for 1 hour. After cooling, the 3-benzylamino-5-methylsulphamyl-4-phenoxy-benzoic acid was precipitated by addition of 4N hydrochloric acid until a pH of 2.5. The precipitate was collected by suction and recrystallized from aqueous ethanol. After drying in vacuo, the melting point of the compound was 231°–233° C.

Example 82

3-Benzylamino-5-dimethylsulphamyl-4-phenoxy-benzoic acid

A. Ethyl 3-benzylamino-5-dimethylsulphamyl-4-phenoxy-benzoate

A mixture of 3-amino-5-dimethylsulphamyl-4-phenoxy-benzoic acid (1.68 g), benzyl bromide (2 g), and ethanol (15 ml) was refluxed for 5 hours. After cooling, the precipitated ethyl 3-benzylamino-5-dimethylsulphamyl-4-phenoxy-benzoate was isolated and recrystallized from ethanol. After drying in vacuo, the compound was obtained with a melting point of 154°–155° C.

B. 3-Benzylamino-5-dimethylsulphamyl-4-phenoxy-benzoic acid

Ethyl 3-benzylamino-5 -dimethylsulphamyl-4-phenoxy-benzoate (1 g) was heated on a steam bath with 1N sodium hydroxide (15ml) for 6 hours. From the resulting solution, the 3-benzylamino-5-dimethylsulphamyl-4-phenoxy-benzoic acid was precipitated by addition of 4N hydrochloric acid until a pH of 2.5. After isolating and recrystallizing from aqueous ethanol, the compound was obtained with a melting point of 205°–206° C.

Ethyl 3-benzylamino-5-(n-butylsulphamyl)-4-phenoxy-benzoate

By substituting in step A above 3-amino-5-butylsulphamyl-4-phenoxy-benzoic acid (1.8 g) for the 3-amino-5-dimethylsulphamyl-4-phenoxy-benzoic acid, the above compound was obtained with a melting point of 149°–149.5° C.

3-Benzylamino-5-(n-butylsulphamyl)-4-phenoxy-benzoic acid

By substituting in step B above ethyl 3-benzylamino-5-(n-butylsulphamyl)-4-phenoxy-benzoate for the ethyl 3-benzylamino-5-dimethylsulphamyl-4-phenoxy-benzoate, and after recrystallization from ethanol, the above compound was obtained with a melting point of 212° C.

Example 83

3-Butylamino-5-(n-butylsulphamyl)-4-phenoxy-benzoic acid

3-Amino-5-(n-butylsulphamyl)-4-phenoxy-benzoic acid was substituted for the 3-amino-4-phenoxy-5-sulphamyl benzoic acid of Example 41. After the saponification, the organic solvents were removed from the reaction mixture by azeotropic distillation. The obtained aqueous solution was adjusted to pH 2.5 by addition of 4N hydrochloric acid. The precipitated 3-(n-butylamino)-5-(n-butylsulphamyl)-4-phenoxy-benzoic acid was isolated by filtration and was several times recrystallized from aqueous ethanol. After drying in vacuo at 115° C, the compound had a melting point of 184°–185° C.

Example 84

4-Anilino-3-benzylamino-5-phenylsulphamyl-benzoic acid

A. Ethyl 4-anilino-3-benzylamino-5-phenylsulphamyl-benzoate

By substituting 3-amino-4-anilino-5-phenylsulphamyl-benzoic acid (1.8 g) for the 3-amino-5-sulphamyl-4-(m-trifluoromethylphenoxy)-benzoic acid of Example 71, the above compound was obtained with a melting point of 165° C.

B. 4-Anilino-3-benzylamino-5-phenylsulphamyl-benzoic acid

Ethyl 4-anilino-3-benzylamino-5-phenylsulphamyl-benzoate (3 g) was dissolved in 1N sodium hydroxide (35 ml), and the solution was heated on a steam bath for 1 hour. After cooling, the reaction mixture was adjusted to a pH of 2.5 by addition of 4N hydrochloric acid. The precipitated 4-anilino-3-benzylamino-5-phenylxulphamylbenzoic acid was collected by suction and recrystallized from acetone/water. The compound was obtained with a melting point of 243° C.

What I claim is:

1. 3-Furfurylamino-4-phenoxy-5-sulphamyl-benzoic acid, a pharmaceutically acceptable salt or ester thereof.

* * * * *

UNITED STATES PATENT OFFICE

CERTIFICATE OF CORRECTION

Patent No. 3,985,777 Dated October 12, 1976

Inventor(s) Peter Werner Feit

It is certified that error appears in the above-identified patent and that said Letters Patent are hereby corrected as shown below:

On the front page of the patent after Item [62] insert:

--[30] Claims priority of British Patent Application No. 61339/68, filed December 24, 1968; British Patent Application No. 30898/69, filed June 18, 1969; and British Patent Application No. 38038/69, filed July 29, 1969.--

Signed and Sealed this

First Day of March 1977

[SEAL]

Attest:

RUTH C. MASON
*Attesting Officer*

C. MARSHALL DANN
*Commissioner of Patents and Trademarks*